United States Patent [19]

Thompson et al.

[11] Patent Number: 5,356,405
[45] Date of Patent: * Oct. 18, 1994

[54] ABSORBENT PARTICLES, ESPECIALLY CATAMENIALS, HAVING IMPROVED FLUID DIRECTIONALITY, COMFORT AND FIT

[75] Inventors: Hugh A. Thompson, Fairfield; Gerald A. Young; Thomas W. Osborn, III, both of Cincinnati; Charles W. Chappell, West Chester; John L. Hammons, Hamilton; James C. Horney, Cincinnati; Lee M. Hines, Wyoming, all of Ohio

[73] Assignee: The Procter & Gamble Company, Cincinnati, Ohio

[*] Notice: The portion of the term of this patent subsequent to Jan. 25, 2011 has been disclaimed.

[21] Appl. No.: 43,645

[22] Filed: Apr. 6, 1993

Related U.S. Application Data

[63] Continuation of Ser. No. 734,404, Jul. 23, 1991, abandoned.

[51] Int. Cl.$^5$ .................... A61F 13/15; A61F 13/20
[52] U.S. Cl. ........................ 604/384; 604/358; 604/366; 604/370; 604/378; 604/385.1
[58] Field of Search ............... 604/358, 366, 368, 370, 604/374, 375, 378, 384, 385.1

[56] References Cited

U.S. PATENT DOCUMENTS

| 810,120 | 1/1906 | Green | 604/378 |
|---|---|---|---|
| 810,127 | 1/1906 | Green | 604/378 |
| 810,129 | 1/1906 | Green | 604/378 |
| 810,130 | 1/1906 | Green | 604/378 |
| 1,352,774 | 9/1920 | Angier | 604/384 |
| 2,662,527 | 12/1953 | Jacks | 128/290 |
| 3,121,040 | 2/1964 | Shaw | 161/177 |
| 3,367,333 | 2/1968 | Scheier | 604/378 X |
| 3,525,337 | 8/1970 | Simons et al. | 604/377 X |
| 3,670,731 | 6/1972 | Harmon | 128/284 |
| 3,680,561 | 8/1972 | Baron | 604/375 |
| 3,860,003 | 1/1975 | Buell | 128/287 |
| 4,054,709 | 10/1977 | Belitsin et al. | 428/224 |
| 4,179,259 | 12/1979 | Belitsin et al. | 425/461 |
| 4,256,111 | 3/1981 | Lassen | 128/284 |
| 4,286,005 | 8/1981 | Berger | 428/167 |
| 4,381,325 | 4/1983 | Masuda et al. | 428/91 |
| 4,578,070 | 3/1986 | Holtman | 604/378 |
| 4,623,329 | 11/1986 | Drobish et al. | 604/29 |
| 4,637,819 | 1/1987 | Ouellette et al. | 604/369 |
| 4,654,040 | 3/1987 | Luceri | 604/385 R |
| 4,662,876 | 5/1987 | Wiegner | 604/380 |
| 4,676,786 | 6/1987 | Nishino | 604/378 |
| 4,701,177 | 10/1987 | Ellis et al. | 604/385 A |
| 4,710,187 | 12/1987 | Boland et al. | 604/385.2 |
| 4,723,954 | 2/1988 | Pieniak | 604/384 |
| 4,747,846 | 5/1988 | Boland et al. | 604/385.2 |
| 4,781,710 | 11/1988 | Megison et al. | 604/378 |
| 4,793,325 | 12/1988 | Sherrod et al. | 604/384 |
| 4,798,603 | 1/1989 | Meyer et al. | 604/378 |
| 4,822,453 | 4/1989 | Dean et al. | 604/375 X |
| 4,834,736 | 5/1989 | Boland et al. | 604/385.2 |
| 4,842,792 | 6/1989 | Bagrodia et al. | 264/130 |
| 4,865,596 | 9/1989 | Weisman et al. | 604/368 |
| 4,868,031 | 9/1989 | Modrak et al. | 428/198 |
| 4,923,454 | 5/1990 | Seymour et al. | 604/371 X |
| 4,950,264 | 8/1990 | Osborn, III | 604/385.1 |
| 4,954,398 | 9/1990 | Bagrodia et al. | 428/400 |
| 5,281,208 | 1/1994 | Thompson et al. | 604/365 |
| 5,314,743 | 5/1994 | Meirowitz et al. | 604/374 |

FOREIGN PATENT DOCUMENTS

| 193309 | 9/1986 | European Pat. Off. | A41B 13/02 |
|---|---|---|---|
| 301874 | 2/1989 | European Pat. Off. | D01D 5/253 |
| 0397110 | 8/1990 | European Pat. Off. | A61F 13/46 |
| 0391814 | 10/1990 | European Pat. Off. | D01D 5/253 |
| 955625 | 1/1950 | France . | |
| 54-151617 | 11/1979 | Japan . | |

Primary Examiner—Randall L. Green
Assistant Examiner—P. Zuttarelli
Attorney, Agent, or Firm—K. C. Johnson; E. K. Linman; J. J. Yetter

[57] ABSTRACT

Absorbent articles, especially sanitary napkins, contain fibers with intra-fiber capillary channels. In-use, the capillary channel fibers direct menses to a storage layer, thereby minimizing product failure and staining of undergarments. The capillary channel fibers can protrude into, or through, a topsheet to provide very aggressive transport of vaginal discharges.

15 Claims, 6 Drawing Sheets

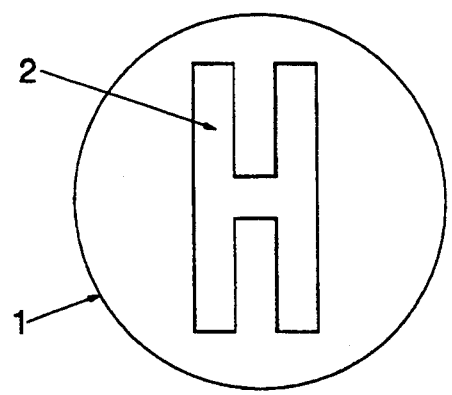
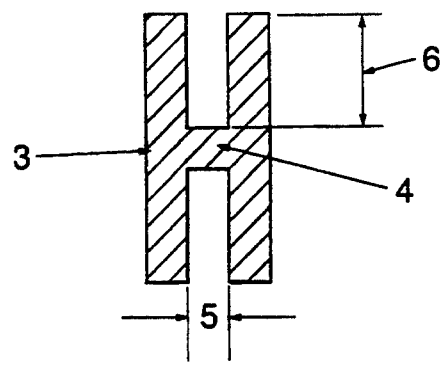
Fig. 1          Fig. 2
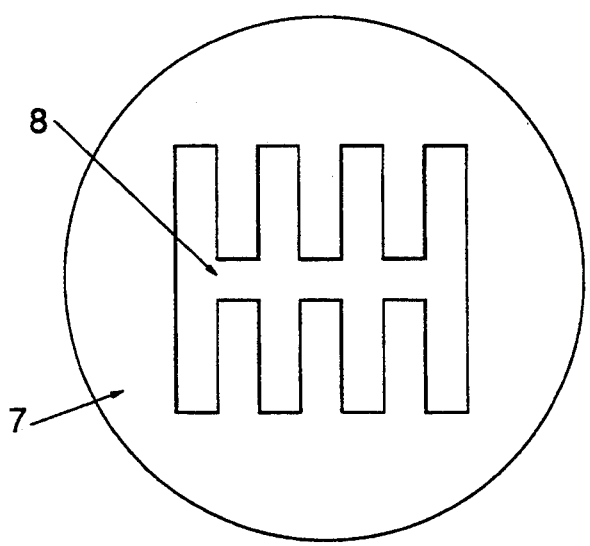
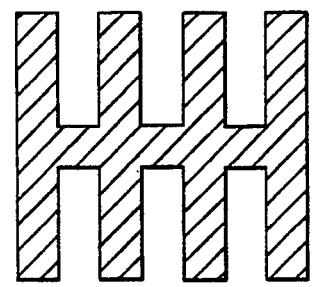
Fig. 4
Fig. 3
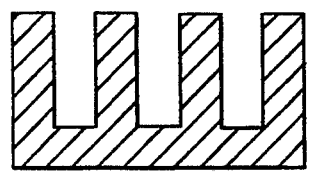
Fig. 5

ABSORBENT PARTICLES, ESPECIALLY CATAMENIALS, HAVING IMPROVED FLUID DIRECTIONALITY, COMFORT AND FIT

This is a continuation of application Ser. No. 07/734,404, filed on Jul. 23, 1991 now abandoned.

TECHNICAL FIELD

The present invention relates to absorbent articles, especially catamenial articles such as sanitary napkins. Such articles are especially adapted for absorbing various body fluids, especially menses, while providing comfort and fit to the wearer.

BACKGROUND OF THE INVENTION

A wide variety of structures for disposable absorbent articles to collect body fluids are known in the art. Commercial absorbent articles include diapers, adult incontinence products, catamenials and bandages. Disposable products of this type comprise some functional members for receiving, absorbing and retaining fluids. Generally, such absorbent articles contain a core of absorbent materials mainly comprising fibrous cellulose. Typically, such articles include a fluid-permeable topsheet, an absorbent core and a fluid-impermeable backsheet.

In the case of catamenial pads, women have come to expect a high level of performance in terms of comfort and fit, retention of fluid, and minimal staining. Above all, leakage of fluid from the pad onto undergarments is regarded as totally unacceptable.

Improving the performance of sanitary napkins continues to be a formidable undertaking, although a number of improvements have been made in both their materials and structures. However, eliminating leakage, particularly along the inside of the thighs, without compromising fit and comfort, has not met the desired needs of the consumer.

Leakage from sanitary napkins is generally attributed to a high concentration of fluid at the point where the menses exits the body and immediately contacts the surface of the napkin. At this point of deposit, the napkin's absorbent material quickly becomes supersaturated. The blood migrates radially from this point and leaks from the sides nearest the wearer's legs. This often results in the smearing of blood on the body and soiling of the undergarments. Attempts to eliminate leakage include: construction of a densified edge to hold the fluid back (U.S. Pat. No. 4,820,295, Chapas et al, issued Apr. 11, 1989); barrier sheets surrounding the article (U.S. Pat. No. 4,666,439, Williams et al, issued May 19, 1987); and "winged" side edges which wrap around the panties (U.S. Pat. No. 4,701,177, Ellis et al, issued Oct. 10, 1987, incorporated herein by reference).

Unfortunately, overdensifying sections of the sanitary napkins detracts from comfort, in-use. Some users are not attracted to the "winged" product, and others are not satisfied with the barrier product. However, since a large part of most absorbent articles remains relatively dry and not utilized, it has now been determined that providing a means to direct fluid from the point of deposit to the areas of the article not fully utilized will avoid super-saturation and considerably reduce or eliminate leakage.

Apart from undergarment soiling, the user of modern sanitary napkins, and the like, has come to expect that the surface of such articles will provide a cleaner, more sanitary and drier aspect than common cloth or nonwoven materials have historically provided. Thus, modern sanitary napkins, diapers and incontinence devices are typically provided with topsheets that are designed to move fluids rapidly through said topsheets and into an underlying absorbent core for storage. As can be envisaged, the more rapid and thorough this movement, the drier and cleaner the surface of the article.

Stated succinctly, the present invention not only provides the desired, directional movement of fluids noted above, which allows improved use of the overall absorbent capacity of the article and less side-leakage, but also provides means to draw fluids through the topsheet, thereby enhancing the desired dry, sanitary benefits, in-use.

Furthermore, the articles which employ the technology embodied in the present invention are more comfortable and better fitting than articles which rely, for example, on highly dense absorbent core regions to achieve fluid movement. Stated otherwise, the technology herein achieves the fluid directionality and handling characteristics available from dense, but uncomfortable, cores in a soft, pliable, low-density and comfortable pad.

It is, therefore, an object of the present invention to provide disposable absorbent articles having improved fluid absorption and retention. It is a further object herein to provide such articles with improved fluid transport away from the skin. It is a particular object herein to provide sanitary napkins and pantiliners with attributes including, but not limited to, improved softness and flexibility, improved fit and improved stain reduction.

These advantages are obtained herein, as will be seen from the following disclosure.

BACKGROUND ART

Disposable articles used to retain human body fluids and waste are well known in the art. U.S. Pat. No. 3,860,003, Buell, issued Jan. 14, 1975, and U.S. Pat. No. 3,670,731, Harmon, issued Jun. 20, 1972, disclose disposable diapers and their manufacture. The diapers disclosed therein contain a significant amount of cellulose material to absorb and retain children's urine and feces.

The technology used in diapers is also used in the field of catamenial products such as pads, sanitary napkins, and pantiliners. Although similar objectives are sought among all the aforementioned products, catamenial products do require some specialized needs for active women as opposed to, diapers for a baby. Minimizing size, improving fit and comfort, and stain inhibition have been the motivation for many of the developments disclosed in the art.

Early patents on disposable catamenials include U.S. Pat. No. 2,662,527, Jacks, Dec. 15, 1953, which discloses a sanitary pad characterized in that it has a portion which at least partially resides outside and within the lips of the wearer's labia. Cellulosic-type fibers are used as the absorbent materials for such pads.

Since Jacks, catamenial pads have been separated into at least two generalized classes. These classes are broken down as pads which have the capability to absorb large or heavy flows of menses and those only intended for small or light flows.

Catamenial articles disclosed in U.S. Pat. No. 4,654,040, Luceri, Mar. 31, 1987, are provided with a "tuck" to produce a body contoured product. The pads disclosed therein can be cellulosic as well as mixtures of cellulosic and polyester/polyethylene conjugate fibers.

The second class of pads, traditionally used for light flows, are exemplified in U.S. Pat. No. 4,701,177, Ellis et al. The pads disclosed therein have a high bulk density, meaning that the fibrous material is tightly compressed together. Normally, these pads are no more than about ⅛ inch thick.

Thinner pads have become increasingly popular. U.S. Pat. No. 4,950,264, Osborn, Aug. 21, 1990, discloses a thin-style sanitary napkin having a body surface and a garment surface wherein the absorbent core is made very flexible by including polymer gelling agents with the fibrous material. These pads have the capacity to handle medium to high menstrual flows.

Polymer gelling agents have been incorporated in absorbent articles in part to achieve a thin profile without sacrificing flexibility; see U.S. Pat. No. 4,662,876, Wiegner, issued May 5, 1987; U.S. Pat. No. 4,865,596, Weisman et al, issued Sep. 12, 1989; and U.S. Pat. No. 4,923,454, Seymour et al, issued May 8, 1990.

One of the keys to the present invention is the use of materials which promote fluid directionality. Various methods to achieve this include formation of a channel patterns to direct fluids; see U.S. Pat. No. 4,781,710, Megison et al, issued Nov. 1, 1988; integration of a web structure in the article; see U.S. Pat. No. 4,637,819, Ouellette et al, issued Jan. 20, 1987, and chemical modification of cellulose fibers; see U.S. Pat. No. 4,256,111, Lassen, Mar. 17, 1981.

EPO Application 391,814, Phillips et al, published Oct. 10, 1990, discloses capillary channel fibers which spontaneously transport liquids and are suitable for use in absorbent articles, wherein the fibers are located near the center of the article. By using the fibers in this matter, fluid can be transported to a larger surface area on the article.

U.S. Pat. No. 4,723,954, Pieniak, Feb. 9, 1988, relates to an absorbent articles comprising a nonwoven fabric facing sheet and an absorbent batt. Some of the fibers of the batt extend into and are integral with the facing fabric. The extended fibers assertedly promote wicking of liquid through the facing and into the batt and stabilize the batt.

U.S. Pat. No. 4,798,603, Meyer et al, Jan. 17, 1989, relates to absorbent articles comprising a hydrophilic absorbent body, a liquid permeable topsheet, a liquid permeable transport layer between said topsheet and said absorbent body, wherein the effective average pore size in said transport layer is smaller than the pore size in the topsheet, and wherein the transport layer is less hydrophilic than the absorbent. The transport layer is configured so that it is capable of attaining a substantially intimate contact with the topsheet and the absorbent body, which is said to be useful for providing an effective fluid communication from the topsheet to the transport layer and from the transport layer to the absorbent body. The transport layer is said to be able to allow a rapid spread of liquid sideways along its lateral length and width dimensions to expose a larger surface area of the absorbent body to liquid.

U.S. Pat. No. 4,973,325, Shetrod et al, Nov. 27, 1990, relates to an absorbent article having a pair of absorbents positioned adjacent to each other. A fluid impermeable baffle and fluid transfer member are said to facilitate the movement of body fluids from the cover downward and outward to distant areas of the absorbents.

EPO Application 397,110, Latimer et al, filed Aug. 5, 1990 relates to an absorbent article comprising a surge management portion of a selected basis weight which is said to rapidly uptake and temporarily hold at least three successive surges of fluids.

French Patent 955,625, Paul Chevalier, "Improvements in Spinning Artificial Fiber", published Jan. 16, 1950, discloses fibers of synthetic origin with allegedly improved capillarity. Chevalier disclosed the primary use of these fibers as absorbing material for making towels, handkerchiefs, bath mats and the like. The fibers are said to have continuous or discontinuous grooves positioned in the longitudinal direction, i.e., parallel to the fiber axis. The fibers may have a central nucleus from which radiate radial leaves. This patent also discloses a process for making the fibers involving a first spinneret for forming the fibers into the desired shape and a second spinneret in direct communication with the first, separated from the first by an insulating plate, for cooling the fiber. The second spinneret is in contact with a cooling element.

U.S. Pat. No. 3,121,040, Gilbert Shaw, "Unorientated Polyolefin Filaments", issued Feb. 11, 1964, discloses a variety of plastic filaments, and a process for making them, which assertedly exhibit good recovery after deformation, and resist orientation (i.e., matting) upon use in such applications as paint brushes. These objects are said to be achieved by preparing fibers having cross-sections consisting of interconnected webs with web length, web thickness, and radius of particular, specified requirements.

U.S. Pat. No. 4,054,709, M. N. Belitsin, et al, "Man-Made Fibre, Yarn and Textile Produced Therefrom", issued Oct. 18, 1977, discloses fibers of polycaproamide and polyethylene terephthalate displaying a cross sectional shape formed of at least two elements formed of intersecting rays which define open capillary channels and a bridge interconnecting particular rays of the elements. The rays intersect at angles of from 10° to 70° to form the capillary channels. The fibers are said to exhibit an appearance and moisture conductivity and absorption approaching natural silk. See also U.S. Pat. No. 4,179,259, Belitsin, which includes some curling disclosure.

U.S. Pat. No. 4,381,325, Yutaka Masuda, et al, "Liquid Retaining Synthetic Fiber, Process for Producing the Same, and Products", issued Apr. 26, 1983 discloses a liquid-retaining synthetic fiber having a substantially pointed free end and a tapered portion. The fibers disclosed include embodiments having a plurality of channels running along the axial length of the fibers.

European Patent Application 88306987.4, publication number 0,301,874, published Feb. 1, 1989, Andrew G. Wilkes and Alan J. Bartholomew, "Cellulosic Fibre", discloses viscous filaments having multi-limbed cross-section, e.g., Y—, X—, H—, and T— shapes which are said to be useful for absorbent products and woven and nonwoven fabrics. U.S. Pat. No. 4,286,005, Richard M. Berger, "Ink Reservoir Element for Use in a Marking Instrument, and Method and Apparatus for Producing Same", issued Aug. 25, 1981, discloses an ink reservoir element formed from a coherent sheet of flexible thermoplastic fibrous material or foam-attenuated extruded polyester fabric, which has been uniformly embossed with a series of parallel grooves. The embossed sheet is compacted and bonded into a dimensionally stable body whose longitudinal axis extends parallel to the embossed grooves.

U.S. Pat. No. 4,623,329, James L. Drobish, et al, "Drainage and Infusion Catheters Having a Capillary Sleeve Forming a Reservoir for a Fluid Antimicrobial Agent", issued Nov. 18, 1986, discloses catheter tubes provided at the inner surfaces with longitudinally extending capillary channels or grooves. The grooves preferably exhibit a favorable surface contact angle for the particular fluid to be dispensed. Surface treatments to alter the surface contact angle can be applied.

Japanese Patent Application 151617-1979, published Nov. 29, 1979, Teijin K K, "Synthetic Fibers", discloses various modified-profile synthetic fibers, especially of polyester or polyamide, having a cross-section shape characterized by fine pores running in the axial direction having diameter of 0.01 microns to 5 microns and a total cross-sectional area of the pores of 0.016 to 50% of the total cross-sectional area of the fibers. The fibers can have additives for increasing water absorption properties.

U.S. Pat. Nos. 4,842,792, issued Jun. 27, 1989, and 4,954,398, Sep. 4, 1990, both to Bagrodia et al disclose the process for making and the polyester fibers made from such a process wherein the fibers have at least one grove wherein the surface of the groove is rougher than the surface outside the groove. Such fibers are used to improve cover, softness, and wetting characteristics of fabrics or yarn made from such fibers.

U.S. Pat. No. 4,868,031, Modrak et al, issued Sep. 19, 1989, discloses soft water-permeable polyolefins nonwovens having opaque characteristics. This invention utilizes fibers having characteristic shapes to improve the opacity and stain-masking properties of cover stocks. The fibers that are disclosed for use in this invention include those having cross-sectional shapes selected from the group consisting of a diamond, a delta, "Y", "X", "O", an oval, a square, a rectangle, and the like.

SUMMARY OF THE INVENTION

In a preferred embodiment, the present invention relates to absorbent articles, preferably a sanitary napkin or pantiliner, but also including diapers, adult incontinence garments, bandages, and the like, comprising:

(a) a fluid permeable nonfibrous formed-film topsheet having a fluid-receiving front face and a back face, said topsheet having multiple openings communicating between said front face and said back face for passage of fluid through said topsheet;

(b) a layer comprising fibers having external intrafiber capillary channels whose widths, on average, are less than the width of the openings in said topsheet, said layer underlying the back face of said topsheet (a) and in fluid-transporting contact therewith;

(c) a fibrous air-laid or wet-laid moisture-absorbing structure underlying said layer (b) and in fluid-transporting contact therewith, said structure comprising multiple, typically cellulosic, non-capillary channel fibers or mixtures of said multiple fibers with absorbent gelling materials, wherein, on average, the width of the spacings between said multiple fibers in the moisture-absorbing structure is less than the width of the capillary channels in the fibers of said layer (b); and (d) a fluid impermeable backsheet underlying said pad (c).

The capillary channel fibers are spontaneously wettable, and are typically hydrophilic or preferably hydrophilized. In highly preferred articles, the capillary channel fibers are positioned such that their channels lie substantially in the machine direction.

In one mode, the contact between the topsheet and the layer of capillary channel fibers is maintained by tensional forces between said topsheet and said layer. In another mode, the contact between the topsheet and the layer of capillary channel fibers is maintained by bonding means. Likewise, the contact between layer (b) and structure (c) can also be maintained by tensional forces or by bonding means.

When the topsheet is a porous, formed film topsheet, the width of the pores is, on average, larger than the width of the intrafiber capillary channels in layer (b). When the topsheet is fibrous, the interfiber spacings are, on average, large than the width of the intrafiber capillary channels in layer (b).

Preferred structures of the foregoing types are wherein the capillary channel fibers are substantially curled, as described more fully hereinafter.

With regard to fluid transport from the topsheet (a) into layer (b), it is preferred that contact between (a) and (b) be so close that a portion of the (preferably curled) capillary channel fibers partially protrude into, or into and through, said topsheet. Likewise, it is also preferred that a portion of the fibers from layer (b) at least partially protrude into structure (c), or that a portion of the fibers from (c) at least partially protrude into (b), since such close contact would also facilitate transport of fluid from (b) into (c). In yet another mode, portions of the fibers in layer (b) at least partially protrude through topsheet (a).

Highly preferred articles wherein moisture-absorbing structure (c) comprises a wet-laid sheet of refined, stiffened, curled (preferably, chemically cross-linked) cellulosic fibers are also provided by this invention.

The articles herein can also comprise a fibrous topsheet. Thus, the invention also encompasses an absorbent article, comprising:

(a) a fluid permeable fibrous topsheet having a fluid-receiving front face and a back face, said topsheet having multiple interfiber openings communicating between said front face and said back face for passage of fluid through said topsheet;

(b) a layer comprising multiple fibers having external capillary channels underlying the back face of said topsheet and in fluid-transporting contact therewith; and (c) a fibrous air-laid or wet-laid moisture-absorbing structure underlying said layer (b) and in fluid-transporting contact therewith, said structure comprising multiple non-capillary channel fibers or mixture of said fibers with absorbent gelling materials.

Preferably, the interfiber spacings which comprise the openings in said fibrous topsheet (a) are, on average, larger than the width of the intrafiber capillary channels in said layer (b). Most preferably, on average, the width of the spacings between said multiple fibers in the moisture absorbing structure (c) is less than the width of the capillary channels in the fibers of said layer (b).

The other considerations mentioned above with regard to the articles having the formed-film topsheet, including, but not limited to, protrusion of the capillary channel fibers into and/or through the topsheet, selection of preferred absorbent cores, etc., also apply to articles having fibrous topsheets.

While the capillary channel fibers employed herein are typically noncellulosic and are conveniently of the polyester type, it will be appreciated that other types of fiber-forming polymers can be used in their preparation. For example, polyalkenes, polyamides, polylactates, poly-dioxanones, and the like, can be used. Since the objective herein is to have the capillary channel fibers direct, rather than absorb, body fluids, it is preferred that the fibers have minimal, or substantially, no, fluid-imbibing (i.e., water-based body fluids) properties. It will be readily appreciated that, if the fibers themselves absorb fluids and swell, the capillary channels could be choked-off. Thus, cellulose derivatives, for example cellulose propionate, cellulose acetate, and the like, also may be used, if desired, only with due regard for the foregoing considerations.

In a preferred embodiment, the absorbent articles herein are prepared in such fashion that at least some of the capillary channel fibers protrude into at least some (preferably, at least about 30%, more preferably, at least about 50%) of the openings in that portion of the topsheet which overlays the capillary channel fibers. In yet another mode, at least some of the capillary channel fibers can be needle-punched or otherwise caused to protrude through at least some (preferably at least about 30%, more preferably, at least about 50%) of the openings in that portion of the topsheet which overlays the capillary channel fibers. In this latter instance, the capillary channel fibers will typically protrude through the topsheet for distances of from about 0.1 mm to about 3 cm. This provides for very active uptake of fluid through the topsheet and into the internal region of the absorbent article.

All percentages, ratios and proportions herein are by weight, unless otherwise specified. The patents and applications mentioned in this document are incorporated herein by reference.

DESCRIPTION OF THE DRAWINGS

FIG. 1 is a direct view of an extrusion die (1) having an orifice (2) of a design suitable for making symmetrical "H" shaped capillary channel fibers having a planar base and capillary channels extending symmetrically from opposite sides of said base.

FIG. 2 is a cross-sectional view of a symmetrical "H" shaped capillary channel fiber (3) with planar base (4), width-between-walls (5) and depth-of-walls (6) made by the extruding a polymer through the die of FIG. 1.

FIG. 3 is a direct view of an alternate extrusion die (7) having an orifice (8) design suitable for making "multiple H" shaped capillary fibers having a planar base and multiple capillary channels extending symmetrically from opposite sides of said base and all optionally having approximately the same channels widths and heights.

FIG. 4 is a cross-sectional view of a capillary channel fiber made by the extruding a polymer through the die of FIG. 3.

FIG. 5 is a cross-sectional view of a multiple " "-shaped fiber.

It is to be understood that FIGS. 1–6C are only for purposes of illustration and are not drawn to scale, inasmuch as the thickness of the walls and planar base of the capillary channel fibers can be, and preferably are, relatively much thinner than the width-between-walls. The thinner the walls and base, the more pliable the fiber, and the higher the fluid capacity.

Figure 6A:
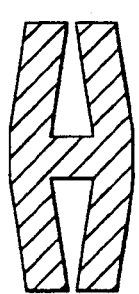
FIG. 6A is a cross-sectional view of an H-shaped capillary channel fiber in a partially collapsed state. While not optimal, such fibers can be used herein.
Figure 6B:
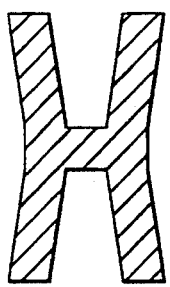
FIG. 6B is a cross-sectional view of an expanded capillary channel fiber. Such fibers can be used herein.
Figure 6C:
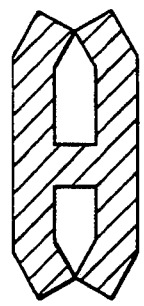
FIG. 6C is a cross-sectional view of a wholly collapsed capillary channel fiber. Such fibers are not used herein.
Figure 7:
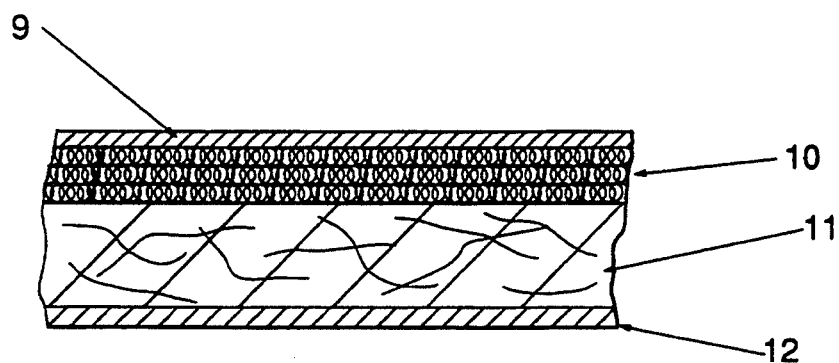

FIG. 7 is a cross-sectional view of a catamenial pad with the view being along the longitudinal axis of the pad. The cross-section shows fluid-permeable topsheet (9), a layer or "secondary topsheet" (10) comprising the capillary channel fibers herein, a fluid retaining core (11), and a fluid impervious backsheet (12).

Figure 8A:
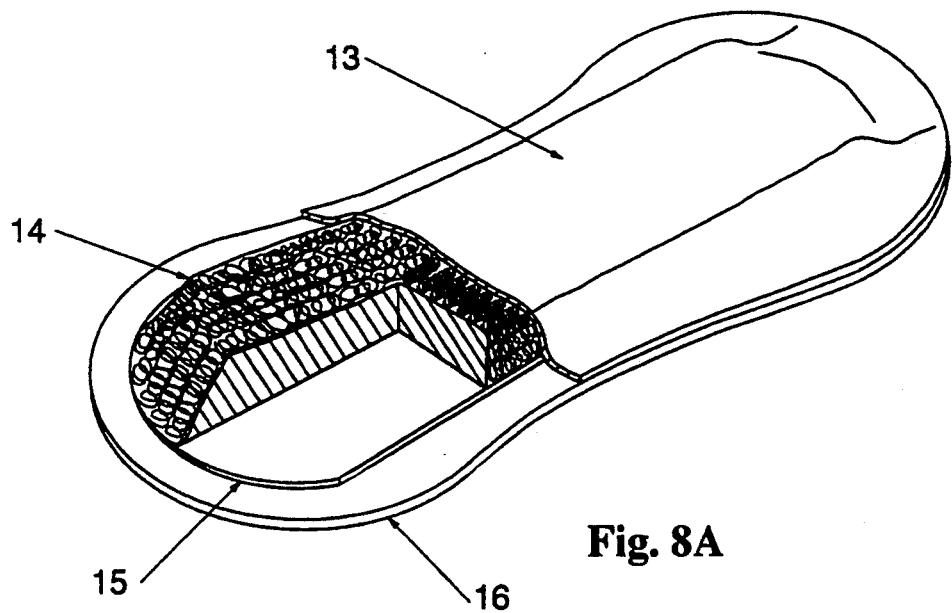

FIG. 8A is a cutaway perspective view of a catamenial pad having a fluid permeable topsheet (13), a fluid distributing capillary channel fiber layer, i.e., as a "secondary topsheet" (14) substantially covering a fluid retaining core (15) and a fluid impervious backsheet (16).

Figure 8B:
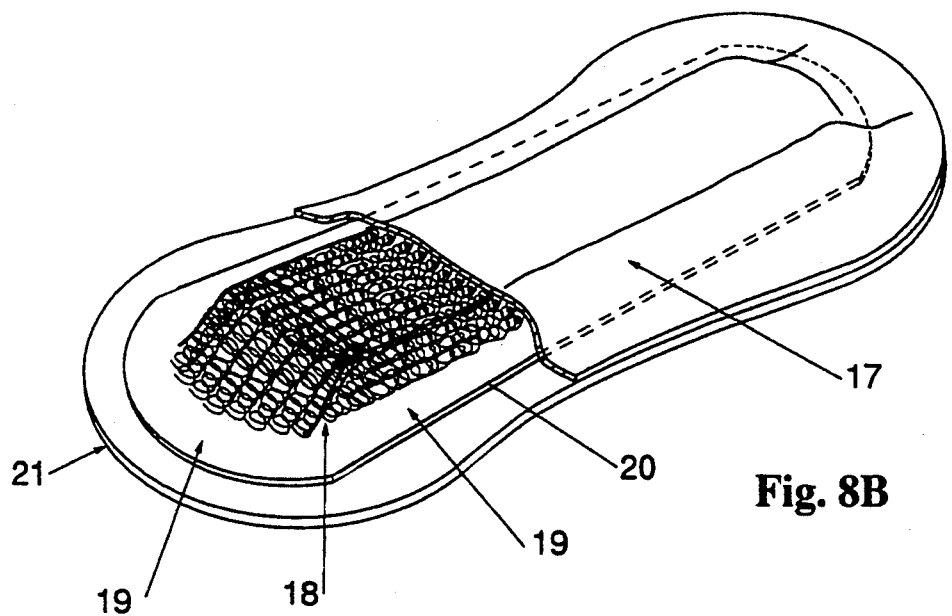

FIG. 8B is a cutaway perspective view of a catamenial pad having a fluid permeable topsheet (17) a capillary channel fiber layer (18) said layer not covering the peripheral edge (19) and terminating about one inch from the end of absorbent core (20). Backsheet (21) is also shown.

Figure 9:
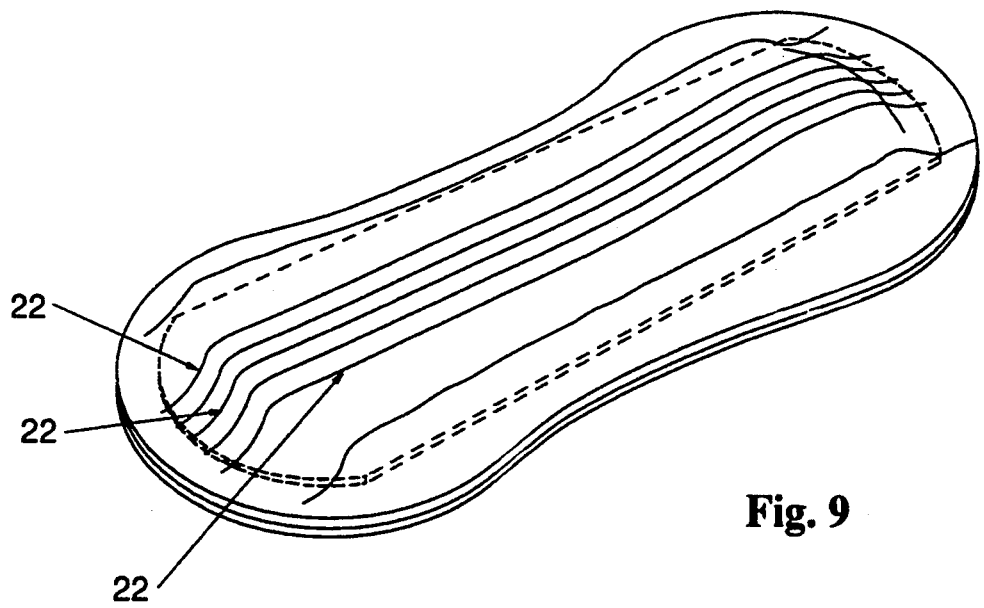

FIG. 9 is a perspective view of a catamenial pad wherein the contact between the various layers is achieved by multiple compression lines (22).

Figure 10:
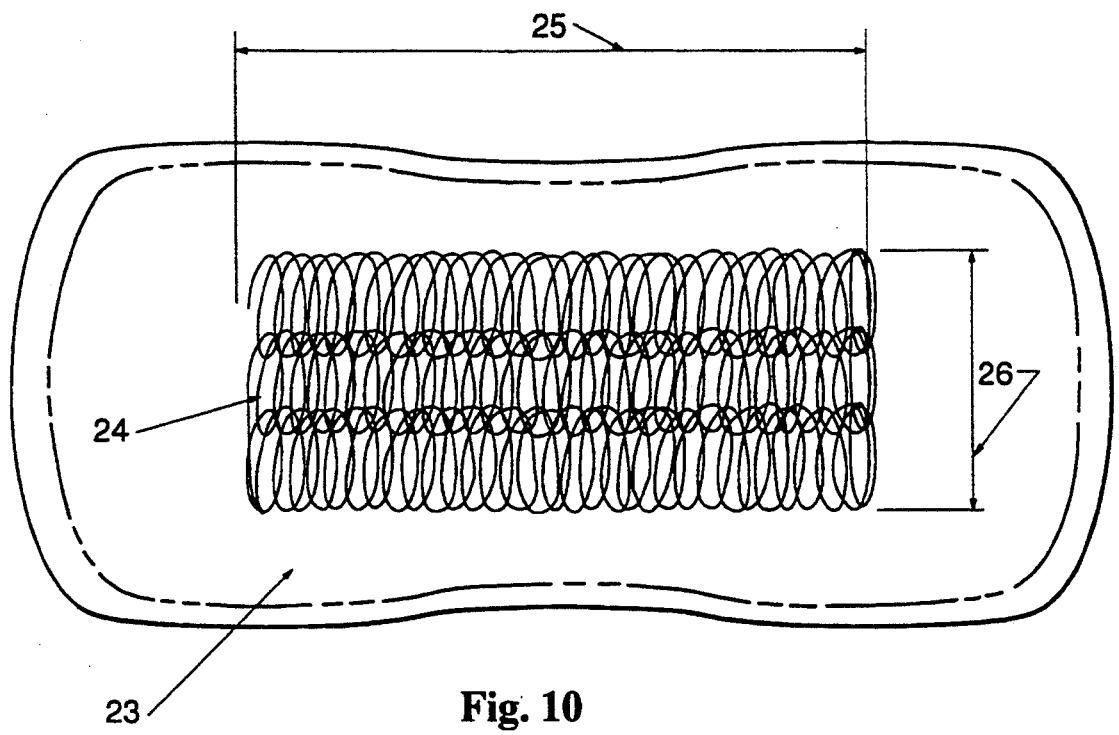

FIG. 10 illustrates the underside of a porous topsheet (23) and the preferred multispiral pattern of glue lines (24) used to affix the topsheet to the layer of capillary channel fibers. The machine direction dimension (25) of the pattern used on a typical catamenial is about 7 inches and the cross-direction dimension (26) is about 2 inches.

Figure 11:
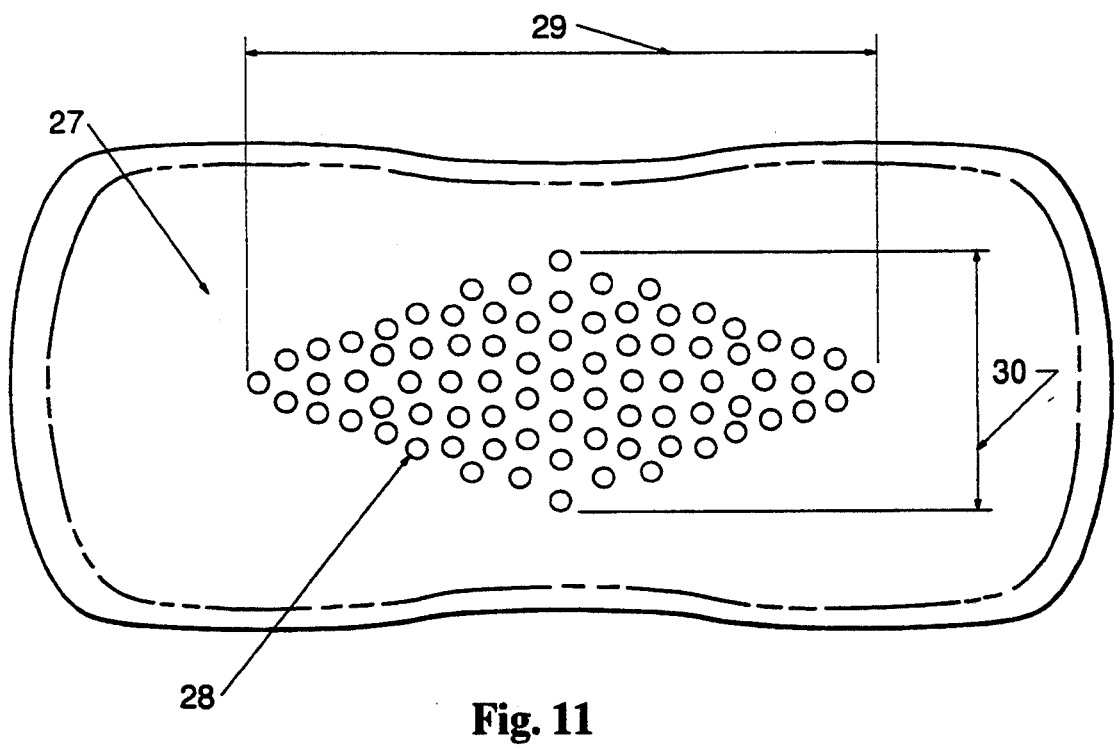

FIG. 11 shows the underside of a porous topsheet (27) and a pattern of adhesive spots (28) having machine direction dimension (29) and cross-direction dimension (30).

Figure 12:
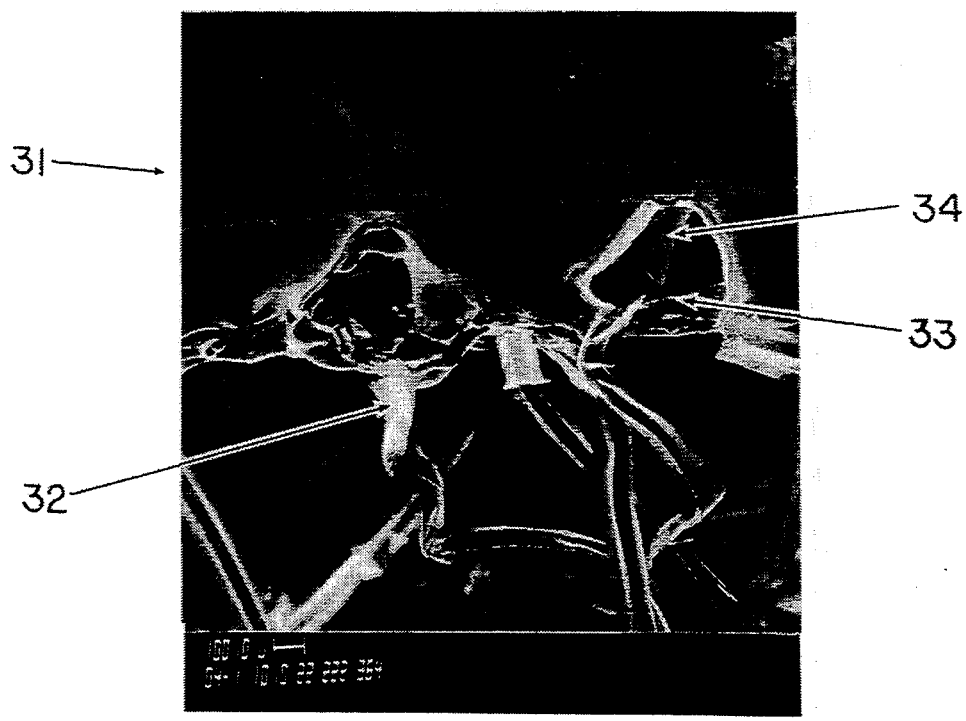

FIG. 12 is a photomicrograph of a section taken of formed film topsheet (31) and the layer of capillary channel fiber (32). The close contact between the capillary channel fibers and the topsheet is shown by the protrusion of capillary channel fibers (33) into pores (34) in the topsheet.

Figure 13:
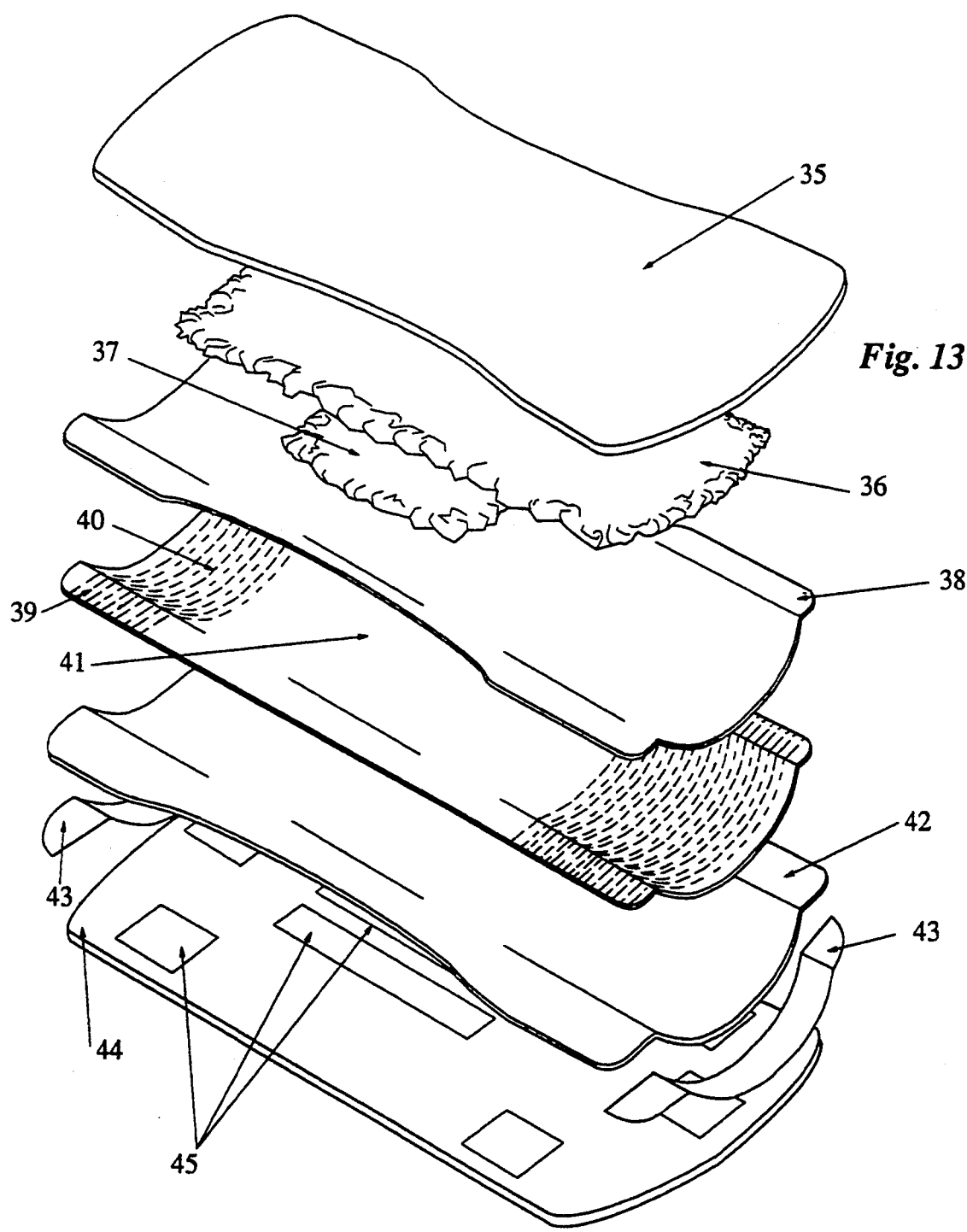

FIG. 13 is an exploded view of the sanitary napkin of Example I, with topsheet (35), a layer of CCF SW194 capillary channel fibers (36), a swatch of CCF SW173 capillary channel fibers (37) underlying layer (36), a creped paper towel (BOUNTY) layer (38), a wet-laid fibrous absorbent core (39) with slitted (40) and unslitted (41) areas and containing absorbent gelling material, backsheet (42) polyethylene end guards (43), optional release paper (44), and showing the relative placement of eight strips of panty fastening adhesive (45). In use, the panty fastening adhesive strips remain on the outer side of backsheet (42) when release paper (44) is removed from the article.

DETAILED DESCRIPTION OF THE INVENTION

As a point of reference, attention is drawn to FIG. 10. In accord with common practice, the long (or "x") axis is referred to as the "machine direction", inasmuch as, during manufacture the articles pass through the machine in the direction of this axis. The short (or "y") axis is referred to as the "cross direction", since it is the direction across the width of the article. The "z" direction is the direction proceeding down through the topsheet, thence into the layer of capillary channel fibers, and thence into whatever fluid storage core that may be provided. The objective is to provide a gradient of capillary suction between the topsheet and underlying layer or layers of the articles herein, such that fluid is drawn in the "z" direction and away from the surface of the article into its ultimate storage layer. Empirically, capillary suction is related to adhesion tension and inversely related to the size of the openings—i.e., in the typical case, the openings in the topsheet will be larger than the intra-fiber capillary channels, which, in turn, will be larger than the inter-fiber capillary channels in a fibrous storage core. The surface hydrophilicity of the components of each layer can theoretically affect the capillary suction gradient.

Simply stated, the capillary channel fibers used herein promote passage of fluids in the "z" direction of absorbent articles. Moreover, by employing a layer of capillary channel fibers whose fibers are positioned to lie substantially parallel to the machine direction, fluid flow in the machine direction is also promoted, which enhances the overall useful absorbency of the article. However, by thus positioning the capillary channel fibers, fluid flow in the cross direction is controlled, thereby minimizing, or even entirely avoiding, leakage of fluid around the lateral edges of the article. Thus, unlike absorbent articles of the prior art which move fluids in an undirected manner in the x, y and z directions by means of fibrous batts which comprise inter-fiber capillary voids, the intra-fiber capillary channels of the fibers herein can be used to provide desirable fluid directionality. Moreover, since the capillary of the fibrous layer of the present invention resides in the fibers, themselves, rather than in inter-fiber spacings, capillarity is not lost when fiber-fiber spacings become displaced. In addition, the capillary channel fiber layer of the present invention provides its fluid drawing and directing functions even when the layer is soft, fluffy and comfortable to the wearer, in contrast to compact, dense and relatively stiff batt materials which function by inter-fiber capillary action. Thus, it will be appreciated that the absorbent articles of this invention function in a substantially different way, using substantially different materials to provide substantially different benefits than the various art-disclosed absorbent structures which do not employ fibers having intra-fiber capillary channels.

It is to be understood that the manufacture of capillary channel fibers of the type employed herein forms no part of this invention. Attention is drawn to EPO Application 391,814 (cited above) or to its co-pending U.S. Continuation-In-Part Application entitled "FIBERS CAPABLE OF SPONTANEOUSLY TRANSPORTING FLUIDS", Ser. No. 07/736,267, filed Jul. 23, 1991, Inventors Phillips, Jones, et al, Eastman Chemical Company, or to the co-pending U.S. Patent Application entitled "OPEN CAPILLARY CHANNEL STRUCTURES, IMPROVED PROCESS FOR MAKING CAPILLARY CHANNEL STRUCTURES, AND EXTRUSION DIE FOR USE THEREIN", Ser. No. 07/482,446, filed Feb. 20, 1990, Inventors Thompson and Krautter, all incorporated herein by reference, for further details regarding means for manufacturing capillary channel fibers.

While a variety of capillary channel fibers can be used herein, the following consideration of various points relating to the preferred capillary channel fibers and their incorporation into the articles of this invention are included for the convenience of the formulator.

I. Fiber Structure and Surface Properties

The fibers used herein can be prepared from any convenient polymer which is nonswelling when wet. Polymers such as polyethylene, polypropylene, polyesters (preferred), and the like, are useful herein, so long as they are spinnable such that they can be formed with external capillary channels, as noted hereinabove. Conveniently, the polymers are melt-extrudable. Typically, the capillary channel fibers herein will be prepared from a synthetic polyethylene terephthalate polymer melt having an inherent viscosity ("IV") of from about 0.6 to about 0.9. (IV is a term of art and can be determined in well-known fashion. See, for example, U.S. Pat. No. 4,829,761 at column 8.) The IV of a polymer melt bears some relationship to the ability of the polymer to retain the shape of the capillary channel walls, and is related to the average molecular weight of the polymers. For example, it is convenient to employ a polyester having an inherent viscosity of about 0.7 herein, but it would be more preferred to employ a polymer having an inherent viscosity of about 0.9, since this would allow the walls of the capillary channels to be thinner, yet sufficiently strong to avoid collapse under in-use pressure. Preferred capillary channel fibers herein have a denier (denier per filament "dpf") of about 10, and capillary channel fibers having such a fine denier, but whose walls are stable, can be achieved especially from polyester having an inherent viscosity of about 0.9. However, in commercial practice using such high IV polymers may require special processing equipment. As a quite acceptable compromise, and in order to achieve capillary channel walls without in-use collapse, polyester/polymer having an inherent viscosity of about 0.7 can be employed at a denier per filament of about 22. However, it is to be understood that the denier of the fibers used is within the discretion of the formulator, and the denier per channel can easily be in the range of 25.

The depth:width ratio of the capillary channels herein is preferably about 2.0, but processing restrictions, as noted above, as well as for economic reasons, a depth:width ratio of about 1.3 is typically employed. Typical and readily producible capillary channel fibers which are quite satisfactory for use herein thus have a depth-of-walls of about 48 microns and a width-between-walls of about 37 microns. The walls, themselves, are typically about 3–15 microns thick. Although variations in these dimensions are acceptable, capillary channel fibers prepared from polyester and having these characteristics are quite effective for their intended purpose. Such fibers can be prepared using conventional operating equipment and readily withstand pressures of the type encountered in sanitary devices, especially sanitary napkins and pantiliners, without collapse or spreading of the capillary channel walls to such an extent that their capillary function is lost.

The capillary channels can be of various shapes. Certain shapes can offer particular advantages in particular product applications. For example,, "U-shaped", "H-shaped", "-shaped" and "V-shaped" capillary channels may be used. The "H-shaped" fibers are one preferred shape. Furthermore, the basic shapes may be repeated (see Figures), or even branched, to produce fibers containing multiple channels, but it will be appreciated that when more than about three repeating shapes are used, some additional stiffness may be noted in the fibers. The multiple " " fibers of FIG. 5 offer the additional advantages of having additional capillarity due to face-to-face contact and being easily curled.

While the polymers used to prepare the capillary channel fibers herein are not, themselves, water-absorbent (nor are they absorbent to urine or blood-containing fluid such as menses), the fibers themselves are most preferably hydrophilic. Since most synthetic polymers are hydrophobic, the capillary channel fibers herein are surface-treated in order to render them hydrophilic. The surface treatment of polymeric fibers involves processes which are well-known in the extensive fiber literature, and such processes can be used herein. In general, such processes involve treating the surface of the fibers with a "hydrophilizing agent", especially a surfactant. (Hydrophilization, which results in wettability of the fibers by aqueous fluids, can routinely be measured, for example, using contact angle measurements. In general, a contact angle less than 90° indicates a hydrophilic surface. A CAHN Surface Force Analyzer (SFA 222) can be used to measure hydrophilicity, as can a variety of other instruments known in the art.) Typical surfactants useful in such processes include various nonionic and anionic detersive surfactants of the general type known in the laundry literature. Hydrophilizing agents include wetting agents such as polyethylene glycol monolaurates (e.g., PEGOSPERSE 200 ML, a polyethylene glycol 200 monolaurate available from Lonza, Inc., Williamsport, Pa., USA), and ethoxylated oleyl alcohols (e.g., VOLPO-3, available from Croda, Inc., New York, N.Y., USA). Other types of hydrophilizing agents and techniques can also be used, including those well known to those skilled in the fiber and textile arts for increasing wicking performance, improving soil release properties, etc. Hydrophilizing agents can be added to the polymer at various stages prior to use, though preferably prior to drawing of the capillary channel fibers to their final size. For example, the hydrophilizing agent can be added in advance to the polymer prior to melting or blended into the polymer subsequent to melting. The additive hydrophilizing agent can also be applied to the polymer subsequent to formation, e.g., subsequent to exit from an extrusion die in a melt, wet, or dry spinning process, preferably prior to drawing of the fiber to small diameter. Of course, since the articles herein are intended to come into contact with sensitive regions of the human body, it is preferred that surfactants used to hydrophilize the surfaces of the capillary channel fibers be nontoxic and nonirritating to human skin. Various surfactant treatments for hydrophilizing the capillary channel fibers are described in the Examples hereinafter. Another method for hydrophilizing fibrous surfaces involves subjecting said surfaces to ionizing radiation, e.g., in a plasma, and such methods have the advantage that there is no surfactant residue on the surface of the fibers. Whatever the means, the overall objective is to secure capillary channel fibers for use herein which are spontaneously wettable by the fluids they are intended to transport.

II. Fiber Morphology

The capillary channel fibers herein have, as noted above and in the Figures, capillary channels on their outer surfaces. While the capillary channel fibers can also have a hollow central core which would provide some additional capillarity, it is preferred that such hollow core fibers not be employed. In general, providing capillary channel fibers with a central hollow core would require the fibers to be somewhat stiffer than desired in order that the core not collapse under pressure. A central core running through a capillary channel fiber would not be expected to quickly pick up fluids, since the fluids would have to find their way to the end of a fiber before proceeding into the core itself. Moreover, a hollow core capillary channel fiber could not release its load of fluid into an absorbent reservoir core without having appropriate contact between the ends of the hollow core fiber and the reservoir core material. To summarize: capillary channel fibers having external capillary channels offer substantial advantages in both pick-up and transfer of fluids, and the provision of a hollow core adds little in the way of performance advantages, but can impact negatively on the comfort level of an article made therewith in contact with the human body.

Moreover, the capillary channel fibers employed herein are preferably not in a straight-line configuration; rather, they are either bent or, most preferably, are in a curled configuration. It is easy to appreciate that capillary channel fibers that are nonlinear have, for a given number of fibers, a higher loft and increased resilience. By increasing the loft of the individual fibers, the overall loft of pads made therefrom is thicker and softer. This allows for the formation of low density, high loft pads which, assuming that the individual fibers themselves are not too thick or stiff (see denier, above), are extremely comfortable, yet effective for transporting fluids.

However, the preferred nonlinear capillary channel fibers herein should not be "kinked". As can also be readily appreciated, kinking a capillary channel fiber can cause points of constriction of the capillary channels at each kinking site. This, of course, would interfere with fluid flow dynamics along said capillary channel.

In addition to the foregoing, there is another substantial advantage to employing nonlinear capillary channel fibers. As indicated in FIG. 12 herein, it is highly preferred that small portions, or "tufts", of the capillary channel fibers actually protrude into at least some of the topsheet orifices of the articles herein. As can be imagined, these protrusions are easier to effect when a high loft capillary channel pad is prepared using curled capillary channel fibers. Even by chance, there is a greater likelihood that a number of ends and/or curls in the capillary channel fibers will find their way into the orifices of the topsheet material than if substantially linear capillary channels were to be employed.

In a preferred mode, the capillary channel fibers herein are "substantially curled" (or otherwise gathered). As is known in the fiber art, fiber curling can be achieved by selectively heat quenching the fibers as they come from their forming die by heating one side of the fibers a bit more than the other side (or, conversely, by cooling one side more quickly than the other). Alternatively, fibers made from synthetic polymers such as polyesters can be curled by stretching, followed by relaxation, or by passing the fiber under tension around a sharp edge, followed by relaxation. Capillary channel fibers can also be curled by immersion in methanol. In a preferred mode, the fibers are substantially helical. Whatever means are used to crimp or otherwise curl the capillary channel fibers, they can, if desired, then be carded to form an assembly of fibers.

The preferred amplitude of the curls is in the range of about 0.1 mm to about 3 mm, and, typically, the frequency of the curls is from about 0.5 per cm of fiber to about 5 per cm of fiber. Fibers with amplitudes of about 3 mm and a frequency of about 0.5 per cm exhibit good softness even in the higher denier ranged fibers having large capillary channels. Stated otherwise, an average capillary channel fiber having a straight-line length of about 2 cm is curled or gathered to provide optimal fibers having a length of from about 0.5 cm to about 1.5 cm.

III. Multifiber Pads

Having thus considered the type of capillary channel fibers employed herein and their individual fiber morphology, the formulator of articles prepared in the manner of this invention will be concerned in the formation of such fibers into absorbent articles. In general, the formulator will be laying-down a bundle of such fibers in the article. In one mode, the fibers can be blown onto, for example, an absorbent core made from cellulosic fibers. In a more preferred mode, multiple capillary channel fibers of the foregoing are formed into a batt or pad, said pad comprising a network of multiple capillary channel fibers. Such multi fiber pads will typically have a caliper in the range from about 0.1 in. (0.254 cm) to about 0.7 in. (1.78 cm), preferably from about 0.1 in (0.254 cm) to about 0.4 in. (1.02 cm) for use in sanitary napkins; preferably from about 0.05 in. (0.127 cm) to about 0.15 in. (0.38 cm) for use in pantiliners; and preferably from about 0.1 in. (0.254 cm) to about 0.5 in. (1.27 cm) for use in infant diapers or adult incontinence garments. For use in disposable absorbent articles, such pads will typically have from about 0.003 g to about 0.016 g of fiber per 1 $cm^2$ surface area, and will have from about 0.003 g to about 0.03 g capillary channel fiber per 1 $cm^3$ volume (measured in the uncompressed state). The amounts of fiber per unit area and per unit volume for pantiliners, diapers and adult incontinence garments can be calculated based on the differences in caliper, noted hereinabove.

Preferably, the denier and strength of the capillary channel fibers will be chosen such that the pad of fibers herein will have a ratio of wet:dry caliper of at least about 80%, more preferably at least about 90%. This ensures that the pad will retain its soft and form-fitting qualities even in use.

Stated otherwise, for a typical sanitary napkin, approximately 1.5 g of curled fibers of the type described herein will provide a rectangular pad having a surface area of about 160 $cm^2$ which is suitable for use as layer (b), i.e., what might be termed a "secondary topsheet", underlying the initial fluid-receiving topsheet of the type disclosed hereinafter.

IV. Use of Multifiber Pads in Absorbent Articles

Having thus described the fibers, the fiber morphology and the inclusion of the fibers into a pad-like structure, the formulator of the absorbent articles herein will now be concerned with the incorporation of such pads into finished absorbent articles. It will be appreciated that the capillary channel fiber pads prepared in the foregoing manner will, themselves, have some amount of holding capacity for fluids, such as menstrual fluids, although this is not their primary function in the present articles. Accordingly, pads made in the foregoing manner can, if desired, comprise the entire absorbent core of, for example pantiliners. However, for most uses, the pad comprising the capillary channel fibers will be used in conjunction with an absorbent core, said core serving as a reservoir for fluids which are transferred from the capillary channel fiber pad into said core. Indeed, most cores will comprise an air-laid felt of cellulosic fibers, or mixtures of cellulosic fibers with absorbent gelling materials. (It will be appreciated by the formulator that such cores are well-known for use in current, conventional disposable articles such as sanitary napkins, diapers, and the like.) Due to the extremely fine structure of the cellulosic fibers in such absorbent cores, the cores exhibit high suctional forces which tend to draw away fluids from the capillary channel fibers and into the core for ultimate storage. This is precisely the intended effect. Thus, for a sanitary napkin, typical cores which comprise from about 1 g to about 5 g of multiple cellulosic fibers and, optionally, from about 0.5 g to about 1.5 g of absorbent gelling material, are overlaid with a capillary channel fiber pad prepared as described above. As fluid proceeds into the article, it encounters the capillary channel fiber network, which distributes the fluid and then surrenders it to the underlying absorbent core, thereby at least partially "renewing" the capillary channel fiber network for the next infusion of fluid. In a preferred mode, the capillary channel fiber pad is used as a "secondary" topsheet under a porous (preferably formed-film) topsheet. Thus, the capillary channel fibers draw fluid through the topsheet, thereby leaving the topsheet with a fresh, dry appearance and feel, then surrender the fluid to the underlying absorbent core, and are thus able to continue the process until the core is saturated.

In a highly preferred mode, the pad of capillary channel fibers is kept in close contact with the overlying topsheet, either by adhesive bonding or by tensional forces, whereby the topsheet and capillary channel pad remain in uniform, close contact. As noted above, contact between the topsheet and the capillary channel fiber pad is, preferably, so close that tufts of the capillary channel fibers extend into the orifices of the topsheet, itself. Likewise, in order to efficiently transfer fluid to the absorbent core, it is preferable that there be close contact (either by adhesive or tensional forces, or by providing a toughened surface of the absorbent core, or by needle-punching some of the capillary channel fibers into the absorbent core) between the capillary channel pad and the underlying absorbent core. Thus, in a highly preferred mode there is an interconnecting network between topsheet, thence into the capillary channel fiber pad, and thence into the underlying absorbent core, whereby fluid efficiently proceeds through the topsheet, along and through the capillary channel pad, i.e., the "secondary topsheet", and into the absorbent core. This interconnection is maintained even in the face of in-use stresses such as moisture, mechanical shear, and pressure-relaxation associated with physical movements of the wearer.

The individual elements used to prepare the articles of this invention are described in detail, hereinafter.

Topsheet

The finished articles herein are provided with a fluid-receiving topsheet. Such topsheets are made of materials which are preferably hydrophobic, but fluid-permeable. Topsheet materials of the type employed in the practice of this invention can be prepared by methods well-described in the patent literature. For example, according to the process of U.S. Pat. No. 4,324,246, Mullane and Smith, Apr. 13, 1982, a sample of thermoplastic material such as 0.0038 cm thick polyethylene film is heated above its softening point. (The softening point is the temperature at which the thermoplastic material can be formed or molded and is less than the melting point of the material.) The heated thermoplastic material in sheet form is then brought into contact with a heated forming screen. The forming screen is preferably an apertured wire mesh screen having the desired aperture size, pattern and configuration. A vacuum is used to draw the heated film against the forming screen, thereby forming the film into the desired pattern and having the desired hole sizes. While the vacuum is still being applied to the film, a jet of hot air is passed over the film. The hot air jet perforates the film in a pattern corresponding to the pattern and size of apertures in the forming screen.

Fluid-permeable topsheets prepared in the manner of the Mullane et al patent are conveniently referred to as "formed films". The caliper of such films is important since, if the caliper is too great, liquid may accumulate in the apertures and not readily pass there through. For the manufacture of absorbent articles such as diapers, catamenials, incontinence articles, and the like, the topsheets typically have a caliper of less than about 0.075 cm, or preferably less than about 0.064 cm.

Another formed-film sheet material useful as the topsheet herein is the resilient, 3-dimensional web exhibiting a fiber-like appearance and tactile impression, comprising a fluid-impervious plastic material, with said web having a multiplicity of apertures, the apertures being defined by a multiplicity of intersecting fiber-like elements, all as disclosed in U.S. Pat. No. 4,342,314, Radel and Thompson, Aug. 3, 1982. The Radel and Thompson sheet materials can be prepared using hydrophobic plastics such as polyethylene, polypropylene, PVC, and the like, and are well-known for use in absorbent products such as catamenials, and the like.

Yet another type of formed-film sheet material useful herein is described in U.S. Pat. No. 3,929,135, Thompson, Dec. 30, 1975, and consists of hydrophobic polymer films having holes which are in the form of tapered capillaries. These "tapered capillary" topsheets are also known for use in absorbent articles, including adult incontinence articles. They may be prepared from various hydrophobic polymers, as mentioned hereinabove; typically, low density polyethylene having thickness of from 0.0025 to 0.0051 cm is employed.

Reference to U.S. Pat. No. 3,929,135 can be made in order to further visualize tapered capillary topsheets. In use, the apices of the capillaries in such tapered capillary topsheets are in contact with the underlying absorbent core material. Generally, tapered capillaries are in the form of a frustrum of a conical surface, but it is to be understood that any generally tapered structure, such as a frustrum of a pyramid or the like with a triangular, square, or polygonal base, is within the term "tapered capillary"; circular tapered capillaries, however, are used in this description for convenience. It is also to be understood that the tapered capillaries can be asymmetric (i.e., the angle of taper on one side can be different from that on another side) and that the angle of taper can change continuously (i.e., be curved) over the distance from base to apex. In the latter case, the angle of taper is defined as the angle of the tangent to the side of the capillary at its point of minimum apex opening dimension. The angle of taper suitable for use in topsheets according to the practice of this invention is from about 10° to about 60°.

Base opening dimension of the capillaries is defined as the maximum open measurement in the plane of topsheet at said tapered capillary. Apex opening dimension is defined as the maximum open measurement in the apex of said tapered capillary, which apex is remote from the plane of the topsheet. When the tapered capillary is in the form of a frustrum of a conical surface, the base and apex opening dimensions are, respectively, the base diameter and the apex diameter. Base diameter and apex diameter are hereinafter used interchangeably with, respectively, base opening dimension and apex opening dimension.

The tapered capillary apex diameter is a diameter which will allow liquid to readily pass from the surface of the topsheet to the underlying absorbent core. The apex diameter is from about 0.004 to about 0.100 inch (0.010 to 0.254 centimeter), preferably from about 0.005 to about 0.020 inch (0.013 to 0.051 centimeter).

The tapered capillary base diameter is selected to satisfy two criteria. The first of these is the subjective feel of the surface of the topsheet which contacts the skin of the user. It has been discovered that polyethylene can be made to exhibit pleasing, cloth-like, non-waxy attributes when the base diameter is within the range from about 0.006 to about 0.250 inch (0.015 to 0.635 centimeter). Preferably, the base diameter should be within the range of from about 0.030 to about 0.060 inch (0.076 to 0.152 centimeter). The second criterion is that the capillary base diameter be small enough to allow an expected liquid droplet to bridge across at least one capillary. This criterion is satisfied by the above dimensions for disposable diapers and sanitary items.

The height of the tapered capillary is defined as the distance between the outermost surface of the topsheet (i.e., that surface which normally contacts the skin of the user) and the apex of the tapered capillary. This height, of course, depends upon apex diameter, base diameter, and angle of taper which have been selected as hereinbefore described. The height of the tapered capillary should provide a structure with a minimum tendency to collapse in use. The characteristics of the material of construction of the topsheet in large measure determine suitable ranges for the height. When the topsheet is low density polyethylene of from 0.001 to 0.002 inch (0.003 to 0.005 cm) thickness and apex diameter and base diameter are in the preferred range, and angle of taper $\alpha$ is in its critical range, the height of the tapered capillary can be from about 0.003 to about 0.159 inch (0.008 to 0.404 centimeter).

A state of relative dryness on the surface of the topsheet implies that most of the liquid which contacts the topsheet is transferred through it to the absorbent element. This in turn implies that each isolated droplet of fluid in contact with the topsheet must be in contact with the base diameter of a tapered capillary. This state of affairs can best be achieved if the land area (the area of the topsheet that exists between the bases of the tapered capillaries) is maintained at a minimum. The minimum limiting value is the case where conical tapered capillaries or pyramid's tapered capillaries are provided in close packed array (where the periphery of the base of each capillary is in contact on all sides with the periphery of the base of adjacent capillaries). The preferred arrangement of minimum land area tends to insure that an individual droplet will contact at least one tapered capillary. A preferred arrangement in disposable diapers is where the tapered capillaries as hereinbefore described are in ordered arrangement with from about 30 to about 1500 tapered capillaries per square inch of topsheet (5 to 231 per square centimeter).

Tapered capillary sheets can be manufactured in any of several ways well known in the art. One particularly suitable method is to provide a heated mold with male elements of the shape and arrangement of the desired tapered capillaries (hereinafter a pin mold). Each male element is secured in such a fashion that its apex extends away from the base of the pin mold. A portion of sheet material is brought into contact with the heated pin mold between the mold and a resilient backing plate. Pressure is applied to the combination of mold, sheet and resilient back plate and tapered capillaries are formed in the sheet to make the tapered capillary topsheet. An alternate way of constructing the topsheet is to subject a portion of liquid-impervious material to vacuum forming over an appropriate mold. After forming tapered capillary sheets in one of the aforementioned ways, it may be necessary to physically remove material from the apices of the capillaries so as to insure that the apex diameters are the desired value. Such removal of material can be accomplished by, for example, subjecting the apices to controlled abrasion or by heating the formed topsheet so as to melt open the apices. See, also, U.S. Pat. No. 4,629,643, Curro and Linman, Dec. 16, 1986, for a microapertured polymeric film with improved tactile impression, which can also be used in the practice of this invention.

A highly-preferred fluid-permeable formed-film topsheet material which can be employed in the practice of this invention is disclosed in U.S. Pat. No. 4,463,045, Ahr et al, Jul. 31, 1984, and reference can be made to that patent to further assist visualization of the Ahr et al structures.

In general terms, the topsheets provided by U.S. Pat. No. 4,463,045 are designed not only to provide a desirable cloth-like tactile impression, but also to substantially eliminate surface gloss. Thus, topsheets made of plastic do not have an undesirably shiny, "plasticky" appearance.

Such highly-preferred topsheet materials can be succinctly described as being a macroscopically expanded three-dimensional plastic "web" having at least one visible surface which appears substantially non-glossy when exposed to light, substantially all of said visible surface exhibiting a regularly spaced, microscopic pattern of discrete surface aberrations, each of said surface aberrations having its amplitude oriented perpendicular to the surface in which said surface aberration originates, each of said surface aberrations having a maximum dimension of less than about 6 mils, as measured in a plane oriented substantially perpendicular to its amplitude, whereby said surface aberrations are not discernible to the normal naked eye when the perpendicular distance between the viewer's eye and the plane of said web is at least about 12 inches, each of said surface aberrations also being free of planar areas which are large enough to inscribe a 4 mil diameter circle and so spaced relative to all adjacent surface aberrations that the maximum diameter of any circle which can be inscribed on any planar surface intermediate said surface aberration and said adjacent surface aberrations on any portion of said visible surface is less than about 4 mils, whereby any light incident upon any portion of said visible surface is diffusely reflected into a multiplicity of directions by said surface aberrations so that said visible surface appears substantially non-glossy.

The '045 topsheet materials can have at least a portion of said surface aberrations comprising protuberances projecting generally outwardly from the surface, and can have at least a portion of said surface aberrations comprising depressions projecting generally inwardly from the surface of said web.

The manufacture of these preferred topsheets can be achieved by use of a forming screen or structure, as generally noted hereinabove, which provides said surface aberrations by virtue of "knuckles" on the support member. (The preparation of such sheets is described in great detail in U.S. Pat. No. 4,463,045, and their method of preparation forms no part of this invention.) In general, the resulting surface aberrations correspond to the knuckles of a woven mesh support structure which directly contacts the visible surface of said plastic sheet during production thereof.

In a preferred manufacturing method, the woven mesh support structure which directly contacts the visible surface of said topsheet is comprised of filaments having a diameter between about one and about two mils and a mesh count between about 160 filaments per lineal inch (2.54 cms) by 160 filaments per lineal inch (2.54 cms) and about 400 filaments per lineal inch (2.54 cms) by 400 filaments per lineal inch (2.54 cms).

Preferred topsheets herein are those wherein said surface aberrations have an average amplitude of at least about 0.2 mils, more preferably at least about 0.3 mils. Most preferably, topsheets having an amplitude of each of said surface aberrations, as measured perpendicular to the surface in which said surface aberration originates, within the range of about ±20%, desirably ±10%, of the average value of the amplitude for all adjacent surface aberrations are used.

"One-way" formed-film topsheets whose backfaces are treated with hydrophilic latex are described in U.S. Pat. No. 4,735,843, Noda, Apr. 5, 1988, and these can also be employed herein.

In addition to the sophisticated apertured materials mentioned hereinabove, the practice of the present invention may also be undertaken with hydrophobic sheet materials having simple holes punched there through.

It will be understood from the foregoing that the aforesaid, preferred, "sheet" or "film" materials used as the topsheet in the practice of this invention are substantially different from fibrous nonwoven materials, which are characterized by a large number of fibers which overlap each other throughout the thickness of the material. Moreover, the topsheet materials used herein are made from materials (preferably, hydrophobic thermoplastic polymeric materials) which provide a clean-appearing, stain-resistant or "non-staining" surface, in use. Such topsheets (as well as fibrous topsheets) can be rendered hydrophilic by spraying on surfactants, e.g., PEGOSPERSE, in well-known fashion.

It will also be appreciated that fibrous, nonwoven topsheets made from materials such as polyethylene, polypropylene and blends are commonly used in commercial sanitary napkins and pantiliners, and such fibrous topsheets can also be used herein.

Such fibrous, i.e., non-formed-film, topsheet materials which can be used herein include, for example, various nonabsorbent fibrous or filamentous network sheets which are aqueous-fluid-permeable by virtue of a multiplicity of holes or channels passing therethrough. Such sheet materials can be prepared by methods well-described in the patent literature. For example, according to the process of U.S. Pat. No. 4,636,419, Madsen et al, Jan. 13, 1987, sheets comprising a network of ribboned filaments of two dissimilar chemical types, and with two dissimilar melting or softening points, are contacted and cooled to allow the formation of a network sheet characterized by said different transverse and longitudinal polymer materials. Such sheets can be used in the practice of this invention.

Another sheet material useful herein is the formaminous net comprising a reticular network of polymeric filaments, said net comprising two arrays of filaments oriented at a displacement angle of 20-90 degrees. Reference can be made to European Patent Application 0215417, filed Jun. 9, 1986, Sneyd et al, to further assist visualization of this sheet. The aforesaid sheet materials can be prepared using hydrophobic plastics such as polyethylene, polypropylene, PVC, and the like, and are well-known for use in absorbent products such as catamenials, and the like. Such sheet materials typically have a basis weight of 0.5-5.0 ounces/yd$^2$ (0.0016 g/cm$^2$-0.016 g/cm$^2$), a caliper of 5-25 mils, an open area of 30-80% and a mesh of 20-40. Conventional nonwoven topsheets can also be employed.

Contact Between Topsheet and Capillary Channel Fibers

An important consideration in the manufacture of the articles herein is to ensure close and sustained contact between the topsheet material and the layer of capillary channel fibers. Such close and sustained contact at the interface of the fiber layer and the topsheet maximizes the fluid acceptance and fluid distribution properties of the finished articles. As noted hereinabove, one method of ensuring close contact is by adjusting the tensional forces between the topsheet and the layer of capillary channel fibers. While effective for its intended purpose, reliance on tensional forces can cause difficulties in manufacture, and can even cause the article to assume a cup-type configuration. Ultrasonic bonding can also be used.

In a preferred mode, close contact between the topsheet and the layer of capillary channel fibers is achieved by means of adhesive bonding. However, even in this mode of operation some care is to be taken to achieve optimal results.

It will be appreciated that using excessive amounts of adhesive can cause the articles to undesirably stick to the body of the user.

It will also be appreciated that using excessive amounts of adhesive could undesirably clog capillary channels in the fibers, thereby diminishing their effectiveness. Accordingly, "noninterfering" amounts of the adhesive are used. Such amounts can vary, depending on the adhesive chosen, the pattern in which it is laid-down, the width of the capillary channels in the fibers, and the like. Controlling the area of adhesive and the diameter of the adhesive lines in the spiral in the manner illustrated also serves to minimize the sticking of the articles to the user's body.

The adhesive should be nonirritating to the skin and otherwise toxicologically-acceptable for use in close contact with delicate body tissues. The adhesive should maintain its bonding properties when moisture is not present, i.e., when the article is being manufactured, and, most preferably, when moisture is present, i.e., when the article is being used.

The adhesive should bond both to the material used to manufacture the topsheet and to the material used to manufacture the capillary channel fibers. If the topsheet or the fibers are surface-treated, e.g., in a hydrophilization process, the nature of the surface treatment will have to be considered when selecting the adhesive.

Typical adhesives useful herein include materials selected from latex adhesives and hot melt adhesives. Fortunately, a great variety of such adhesives are well-known in the art, and by giving appropriate attention to the factors mentioned above, the manufacturer can select an appropriate adhesive for any set of circumstances. In order to sustain good contact when the article is in use, i.e., becomes moistened by body fluids, it is preferred that the adhesive be insoluble in body fluids.

Having thus considered the general nature of the parameters which must be considered when bonding the topsheet to the layer of capillary channel fibers, the following illustrates preferred materials and techniques for use in the practice of this invention.

While the adhesive can be laid down in a random pattern, it is most preferred that a spiral, or multiple spiral, pattern, such as the one illustrated in FIG. 10, be used. Alternatively, the spot pattern of FIG. 11 can be used, but is less preferred.

In a preferred mode, the lines of adhesive are applied in the spiral pattern using a 0.2 mm nozzle, but application using nozzles at least as large as 0.6 mm is satisfactory.

The selection of adhesive can vary with the needs of the formulator, but the following points are instructive. Experience has shown that, in general, latex adhesives tend to be somewhat less satisfactory than hot melt adhesives. Adhesives available from Findley Adhesives, Inc., especially hot melt adhesive 4031, but also, almost uniquely, latex 8085, are useful herein. (Note: Findley H-4031-01 is hydrophobic, which may account for its good performance properties. By contrast, latex H-8082-05 is hydrophilic and may undesirably separate when wetted under in-use conditions.) A variety of hydrophilic finishes can be present on the capillary channel fibers, and the type of adhesive can vary somewhat, depending on the finish used, and its usage level. As noted, the objective is to ensure good contact between the topsheet and the layer of capillary channel fibers at all times, thus maximizing fluid acceptance and partitioning properties. With the Eastman capillary channel fibers such as SW194, Eastman's finish LK 5570 (49% PEG 400 monolaurate/49% PEG 600 monolaurate/2% 4-cetyl-4-ethylmorpholinium ethosulfate [antistat]) works best with Findley adhesive 4031 at high, medium and low (0.78-0.87; 0.38-0.57; 0.28-0.33 wt. percent of fiber) finish levels. Typically, about 0.07 g, 0.08 g or 0.05 g, respectively, of Findley 4031 (depending on high, medium or low finish level) gives excellent adhesion.

Other finishes herein include Eastman's LK 5483 (70% PM [PEG 600 monolaurate, polyoxylaurate (13.64) monolaurate]/30% potassium lauryl phosphate), Eastman's LK 5563 (45% PEG 400 monolaurate/45% PEG 600 monolaurate/10% 4-cetyl-4-ethylmorpholinium ethosulfate) as well as the polymer available as MILEASE T, which is well-known in the detergency arts (see, for example, U.S. Pat. No. 4,132,680) as a fiber-coating ethylene terephthalate/polyethyleneglycol terephthalate soil release polymer, and which is available from ICI Americas.

As noted, the amounts of adhesive employed will vary, but typically range from about 0.05 g for a 2 in.×5 in. spiral pattern to about 0.07 g for a 2 in.×7 in. spiral pattern, using a hot melt adhesive. For a latex adhesive, from about 0.1 g to about 0.15 g for a 2 in.×5 in. pattern will suffice. For the spot pattern, about 0.05 g is used in an area of ca. 2 in.×5 in.

Close contact between the topsheet and the underlying layer of capillary channel fibers can be further improved by applying pressure during the gluing process and/or by "combing" the uppermost capillary channel fibers in the layer to provide individual fiber protrusions which give better contact with the adhesive.

Irrespective of the bonding method employed, means for judging the contact between the topsheet and the underlying layer of capillary channel fibers relate to the speed with which fluid impinging on the topsheet is drawn into the capillary channel fiber layer. Various means for judging transported fluid through the topsheet and into the capillary channel fiber layer can be envisioned. However, a simple Drop Test is conveniently employed. In this Test, sheep's blood or any desired type of artificial menses is allowed to come to room temperature while stirring at a gentle speed. With a catamenial pad laying horizontally, the pad is visually sectioned into horizontal thirds. Using a dropper held approximately ½ in. above the pad, add 4 individual drops of blood onto the topsheet of the top third of the pad and add drops toward the middle of the pad at 1 in. intervals. Simultaneously, start the timer at the addition of the first drop of blood or artificial menses. Record, in seconds, the time it takes each drop to penetrate the topsheet. Repeat the drop addition with 3 drops added to the middle third of the pad. Repeat the blood addition with 4 individual drops being added to the bottom third of the pad. Average the readings. Any descriptors selected by the formulator can be used to denote the speed of movement through the topsheet into the underlying layer of capillary channel fibers, and it will be appreciated that such descriptors will vary with the standards employed by the formulator. A score of Excellent can be attributed to fluid movement through the topsheet and into the capillary channel layer in 1–10 seconds; a score of Good for fluid movement in a period of 10–15 seconds; a score of Fair for movement in 15–20 seconds; and a score of Poor for periods of time greater than 20 seconds.

In general, for sanitary napkins employing the formed-film topsheet according to U.S. Pat. No. 4,463,045, the layer of preferred capillary channel fiber materials disclosed herein and the spiral gluing (hot melt) pattern of FIG. 10, the movement of fluid through the topsheet and into the capillary channel fiber layer is judged to be Excellent-to-Good using the above Drop Test.

Absorbent Core

Typically, finished absorbent articles will contain sheets or batts of fibrous absorbent material such as cotton fluff, cellulose pulp, chemithermomechanical pulp, and the like, well-known in commercial practice. As is quite well-known from recent commercial practice, cores which also comprise absorbent gelling materials (sometimes referred to as "super-sorbers") are becoming broadly used in absorbent articles. Especially preferred absorbent gelling materials are the polyacrylates and acrylic acid grafted starch. The manufacture of such wet-laid and air-laid absorbent cores is a routine matter. Various fluid-absorbing sponges, peat moss, cotton, cloth, and the like, materials are also usable herein.

A particular type of absorbent core is preferred for use herein. In this type of core, curled, twisted, preferably chemically stiffened and crosslinked, cellulose fibers are refined to provide fibers which can be used in sheet form as the absorbent core. The preparation of suitable curled, chemically stiffened cellulosic fibers from which one can prepare the refined, curled, chemically stiffened cellulosic fibers used in the practice of this invention is described in great detail in U.S. Pat. Nos. 4,888,903; 4,822,543; 4,889,595; 4,889,597; 4,889,596; and 4,898,642, incorporated herein by reference. Use of such fibers in combination with absorbent gelling materials, and means for manufacturing such combinations, are described in U.S. Pat. No. 4,935,022. Such preparations typically involve the use of aldehydes, such as glutaraldehyde, as crosslinking agents. In addition, polycarboxylic acids can be used as crosslinking agents. (It will be appreciated that other means for preparing other crosslinked cellulosic fibers are also known, and such fibers may also be used herein, although the fluid absorbency properties may be suboptimal as compared with the above-mentioned fibers. Reference can be made to the various citations in U.S. Pat. No. 4,898,642 and PCT U.S. 89 01581 for other fiber types.) Once in hand, the curled cellulosic fibers are refined to provide the fibers used to prepare the preferred absorbent cores used in the practice of this invention.

Backsheet

The backsheet is conventional, and can comprise a fluid-impermeable polymer sheet, for example polyethylene or polypropylene, that is thin enough to be flexible. A polyethylene sheet 0.001–0.5 mm thick is typical. Flushable or biodegradable backing sheets can also be used, e.g., with pantiliner devices herein.

Optional Retaining Means

The absorbent structures herein can optionally, but preferably, be provided with means to hold them in place on or near the user's body to allow the structures to perform their intended function. For example, sanitary napkins can be provided with glue stripes facing outward on their backsheet in well-known fashion. Various pins, clips and fasteners of well-known types can optionally be employed.

The following Examples further illustrate the practice of the invention, but are not intended to limit the absorbent articles encompassed therein.

EXAMPLE I

THICK PAD

A sanitary napkin article is hand-made using the following components. Reference is made to FIG. 13 for the assembly of the product.

The specifications of the finished product are as follows.

| Parameter | Specifications |
|---|---|
| Pad weight (g) | 9.82 ± 0.12 |
| Core weight (g) laminate only | 2.57 ± 0.04 |
| Pad length (mm) | 226 ± 1 |
| Core length (mm) | 197 ± 1 |
| Pad width at center (mm) | 81 ± 2 |
| Core width at center (mm) | 70 ± 0 |
| Pad caliper (inches at 0.13 psi) | 0.611 ± 0.02 |
| Core caliper (inches at 0.13 psi) | 0.058 ± 0.003 |
| Seal length (mm) | 8 ± 1 |
| Components | |
| Polyethylene ring rolled formed-film topsheet (according to U.S. Pat. No. 4,463,045) | ca. 9"× 5" |
| Capillary channel fibers SW194 (Eastman) | 1.5 g |
| Capillary channel fibers SW173 (Eastman) | 0.5 g. |

-continued

| | Specifications |
|---|---|
| Findley extended adhesive backsheet (Formula #198-338) | 9" × 5" |
| Creped BOUNTY paper towel | Shaped* |
| Panty fastening adhesive | Six ¾" × ¾" pieces; two ¾" × 2.5" pieces |
| Release paper | As needed |
| Surfactant (PEGOSPERSE) | 0.01 g |
| White poly for ends | 4" × 0.75" |
| Absorbent gelling material (AGM) slit core non-slit central area; total core wt. 2.6 g; contains 0.7 g polyacrylate AGM | 70 mm × 193 mm with 2¾" non-slit center area |
| Findley Adhesive-4031 | 0.05 g |

*See FIG. 13(38) for shape. The shape is designed to provide anatomical fit.

The SW194 fibers are of the H-shaped cross section having a denier of approximately 22 dpf, a channel width of about 37 microns and a channel depth of about 48 microns. The SW173 fibers comprise a carded staple sliver which has been stuffer box crimped to 7.8 crimps per inch and are in the preferred H cross section, with a channel width of 38 microns and a channel depth of 19 microns. Capillary channel fibers SW194 are 6 in. long and capillary channel fibers SW173 are 2 in. long.

In the making procedure, the ring rolled topsheet is cut to the desired size, a template (2"×7" opening) is placed on the back side of the topsheet and sprayed with the Findley 4031 adhesive. The adhesive is applied in a spiral pattern (see FIG. 10). The layer of capillary channel fibers SW194 is hand-pressed in the center of the glue sprayed area. The fibers run parallel to the long axis of the article. Capillary channel fibers SW173 are hand pressed as a swatch (with fibers parallel to the long axis of the article) in the center of the layer capillary channel SW194 fibers. This provides a Pre-Assembly of the topsheet and capillary channel fibers.

For convenience, the following procedure is carried out using a concave forming die. The Findley adhesive backsheet (polyethylene backsheet with adhesive coating and release paper) is placed in the form. The AGM slitted core is placed over the backsheet, and the creped tissue (BOUNTY) is placed over the AGM core. The Pre-Assembly, prepared above, is placed over the creped tissue, as shown in FIG. 13. With the Pre-Assembly over the creped tissue, the article's components are pulled snugly over the edges of the form, but not so tightly that the components begin to pull away from the form. Firm pressure is applied to adhere the edges with the adhesive on the backsheet. The article is removed from the form and the ends are pressed in place using a roller. The release paper is peeled from the back of the backsheet. The end guard polyethylene strips are added and the strips of panty fastening adhesive are placed on the article. The outer surface of the topsheet is sprayed with 0.01 g of PEGOSPERSE surfactant.

EXAMPLE II

THIN PAD

Reference is made to FIG. 13. The assembly of the thin pad is equivalent, except that CCF SW173 fibers are used in place of the layer of CCF SW194 fibers (36), and no swatch (37) of fibers is used.

Assembly of the product is as follows. Cut capillary channel fibers (CCF SW173) to 7 in. length; 0.75 g fibers used. Cut the ring-rolled topsheet to size. Place the template on the bottom side of the topsheet and apply Findley 4031 adhesive (spiral pattern). Handpress CCF SW173 fibers in the center of the glued area with the fibers running substantially parallel to the long axis of the topsheet. Lay the Findley backsheet on flat surface. Place the slitted AGM laminate core on the Findley Backsheet. Center the S2 die shaped tissue over the laminate core. Center the topsheet/capillary channel fiber Pre-Assembly over the creped tissue. Secure the Pre-Assembly and smooth at edges. Roll the edges to seal. Peel the release paper from the back of the pad. Tear and remove in 2 or 3 pieces, then place the poly on the ends of the article. Place the PFA on the pad. Spray the topsheet with PEGOSPERSE; 0.01 g.

The specifications of the finished product are as follows.

| | Specifications |
|---|---|
| Parameter | |
| Pad weight (g) | 8.50 ± 0.18 |
| Core weight (g) laminate | 2.54 ± 0.09 |
| Pad length (mm) | 232 ± 4 |
| Core length (mm) laminate | 201 ± 1 |
| Pad width at center (mm) | 85 ± 1 |
| Core width at center (mm) | 65 ± 1 |
| Pad caliper (in. at 0.13 psi) | 0.211 ± 0.005 |
| Core caliper (in. at 0.13 psi) | 0.074 ± 0.003 |
| Components | |
| Polyethylene formed-film topsheet (ring rolled; per U.S. Pat. No. 4,463,045) | 9" × 5" |
| Capillary channel fibers SW173 (Eastman) | 0.75 g; 7" length |
| Findley extended adhesive backsheet (Formula #198-338) | ~9" × 5" |
| Creped BOUNTY paper towel | Shaped* |
| PFA (panty fastening adhesive) | Six ¾" × ¾" pieces and two pieces |
| Release paper | As needed |
| PEGOSPERSE | 0.01 g |
| AGM slit core non-slit center; total core weight 2.5 g; contains 0.7 g AGM | 65 mm × 193 mm with 2¾" non-slit center |
| Findley 4031 (adhesive) | 0.05 g |

*As in Example I.

In the following Examples III and IV, the capillary channel fibers are used in absorbent articles whose absorbent cores comprise refined, curled cellulosic fibers. The manufacture of such refined absorbent fibers forms no part of this invention. Further details regarding their manufacture are described in the concurrently-filed U.S. Patent Application entitled "Absorbent Core for Use in Catamenial Products", Ser. No. 07/734,405, filed Jul. 23, 1991, Inventors Buenger, Homey and Hammons, incorporated herein by reference. For the convenience of the formulator, the manufacture of such fibers, means for refining the fibers and means for forming said refined fibers into absorbent sheets are described hereinafter.

Fiber Manufacture

The curled fibers prepared in the manner described in the above-cited references comprise individualized curled cellulosic fibers which are preferably chemically stiffened by means of a crosslinking agent. As described in U.S. Pat. No. 4,898,642, such curled fibers have an average dry fiber twist count of at least about 4.5 twist nodes per millimeter an average wet fiber twist count of at least about 3.0 twist nodes per millimeter and at least about 0.5 twist nodes per millimeter less than said dry fiber twist count; an average isopropyl alcohol retention value of less than about 30%; and an average water retention value of between about 28% and about 50%. Highly preferred fibers have an average dry fiber curl factor of at least about 0.30, more preferably at least about 0.50. It is to be understood that the refining process herein does not substantially affect the foregoing parameters, inasmuch as the process is carried out in such a manner that there is little or no defibrillation of the original curled and twisted fibers. Rather, the original fibers are, in general, reduced in length. On average, the original curled fibers employed herein have lengths ranging approximately from about 1.6 mm to about 7 mm. After refining in the manner disclosed herein, at least about 30% of the resulting fibers, preferably at least about 50%, more preferably about 90% of the refined fibers have an average length which is from about 20% to about 40% of the length of the original, unrefined curled fibers. Stated otherwise, on average the unrefined fibers prepared by the above-referenced processes will have lengths in the range from about 1.6 mm to about 7 mm, whereas, after refining, the lengths of the fibers will typically be mainly in the average range from about 0.25 mm to about 1.5 mm.

Fiber Refining

Once prepared by any of the aforementioned, art-disclosed processes, the curled cellulosic fibers are refined to provide the fibers used in the practice of this invention.

In a typical process, an aqueous stock comprising about 3% by weight of said fibers and 97% by weight water is passed through a Sprout-Waldron (now available as Sprout-Bauer) single disk refiner (available from Koppers Company, Inc., Muncy, Pa., Model 105A-LAB) using a deknotting disk of the 17804-A type. Importantly, it is the objective of the refining process herein to cut the twisted fibers without substantially defibrillating them.

The 3% aqueous stock solution is diluted to 0.5% consistency and flows through the Sprout-Waldron refiner using a gap setting of from about 5 mils to about 30 mils, preferably about 2.5 mils. (Note: The Sprout-Waldron is modified by removing the equalizing spring so that the gap setting remains constant throughout the flow of the fibrous stock solution.) Typical flow rate is 9-10 gallons per minute and the refining amperage is about 45 on a 25 hp. motor. (Use of the amperage term is a measure of the mechanical energy imparted to the fibers during the refining.) A single pass of the fibers through the gap is employed.

In an alternate mode, the curled cellulosic fibers can be used in combination with crill, which is a highly refined southern softwood kraft fiber having a Canadian standard freeness between about 50 to about 100 ml. (TAPPI standard). Typically, the crill comprises up to about 5%-10% by weight of the curled cellulosic fibers. Addition of crill can impart desirable strengthening properties to the final sheets, and also can serve as a diluent in the sheets, for reasons of economy.

Following the refining step, the 0.5% aqueous slurry of the refined, twisted fibers is further diluted to a slurry weight of from about 0.1% -0.2% for use in the Sheet Formation operation, hereinafter.

Sheet Formation

In general terms, the formation of the above-prepared refined, curled cellulosic fibers into sheets suitable for use as the absorbent core in catamenials, and the like, employs a Fourdrinier papermaking process with a standard fixed roof forming technique, and involving vertical transfer of the sheet across a through-air dryer. See, for example, U.S. Pat. No. 4,889,597. In the process, a breast roll is employed in the manner known in the art for preparing facial tissue, filter paper, and the like. However, unlike the manufacture of filter paper, the sheet herein is dried without substantial pressure; rather, the through-air dryer system is employed.

In more detail, the above-described aqueous slurry comprising from about 0.1% to about 0.2% by weight of the refined, twisted cellulosic fibers is introduced from the head box of the papermaking machine onto a standard forming wire. An objective is to avoid fiber flocculation, which would result in a nonuniform laydown of fibers in the resulting sheet. The distance between the top of the head box and the forming wire (the "slice setting") is preferably set at about 90 mils to avoid flocculation. The dilution water can also be adjusted to avoid flocculation by settling. As noted, avoiding flocculation results in sheets having a substantially uniform distribution of fibers.

Dewatering of the sheet is relatively rapid down to the 23% level. A vacuum box is employed to remove any excess water from the forming wire, after which the sheet is transferred to a drying fabric. Drying is accomplished using a standard through-air dryer with an air temperature of about 300° F. This results in a sheet having about 3%-4% by weight moisture, which can requilibrate (depending on ambient humidity) to 8%-10% moisture. It should be noted that the sheet is preferably not compacted during drying, since this interferes with the absorbency capacity. While the sheet formed in the foregoing manner is quite absorbent and suitable for use in many absorbent structures, it will be appreciated that such sheets may be somewhat stiffer than desired by the formulator of sanitary napkins and pantiliners. Using standard techniques, the sheets can be calendered and/or passed through rollers in an "S" configuration to flex the sheet to the point that it becomes soft and pliable to the touch. This can be repeated, according to the desires of the formulator.

It is to be understood that the sheets prepared in the foregoing manner are highly absorbent and quite suitable for use in catamenial products. However, the sheets may lack strength for some purposes, especially when moistened and subjected to stresses, e.g., during wear by the user. In order to overcome this problem, it has been determined that a thin scrim of commercially available nonwoven, extremely porous, very low basis weight polypropylene, such as AMOCO D2 scrim, for example, can be laid down on the forming wire of the Fourdrinier, after which the refined, curled fibers are formed into a sheet on top of the scrim. During formation of the sheet on such a scrim, small amounts of the fibers pass through the scrim and attach the sheet to the scrim by a phenomenon referred to in the art as "stapling" Preparing the sheet/scrim by this process is preferred over the alternative process which would involve forming the sheet, placing the scrim on top of the sheet, and subjecting the resulting scrim/sheet to vacuum. In this latter type of process it has been noted that good "stapling" does not occur, and the scrim tends to decouple from the sheet.

Fiber A

Fibers prepared according to the procedure of EXAMPLE I of U.S. Pat. No. 4,898,642 are refined in the foregoing manner. The slurry of refined fibers is formed into a tissue sheet having a Basis Weight (weight per 3,000 ft.$^2$) of 35 pounds. The sheet can be used, for example, in a tissue laminate having a central layer of polyacrylate absorbent gelling material. Such laminates typically comprising about 0.68 grams of the absorbent gelling material are useful as the absorbent core in ultra-thin sanitary napkins of the type provided by the present invention.

Fiber B

Individualized, crosslinked fibers are made by a dry crosslinking process utilizing citric acid as the crosslinking agent. The procedure used to produce the citric acid crosslinked fibers is as follows:

1. For each sample, 1735 g of once dried, southern softwood kraft (SSK) pulp is provided. The fibers have a moisture content of about 7% (equivalent to 93% consistency).
2. A slurry is formed by adding the fibers to an aqueous medium containing about 2,942 g of citric acid and 410 ml of 50% sodium hydroxide solution in 59,323 g H$_2$O. The fibers are soaked in the slurry for about 60 minutes. This step is also referred to as "steeping". The steep pH is about 3.0.
3. The fibers are then dewatered by centrifuging to a consistency ranging from about 40% to about 50%. The centrifuged slurry consistency of this step combined with the carboxylic acid concentration in the slurry filtrate in step 2 set the amount of crosslinking agent present on the fibers after centrifuging. In this example, about 5 weight % of citric acid, on a dry fiber cellulose anhydroglucose basis is present in the fibers after the initial centrifuging. In practice, the concentration of the crosslinking agent in the slurry filtrate is calculated by assuming a targeted dewatering consistency and a desired level of chemicals on the fibers.
4. Next, the dewatered fibers are defibrated using a Sprout-Waldron 12" disk refiner (model number 105-A) whose plates are set at a gap which yields fibers substantially individualized but with a minimum amount of fiber damage. As the individualized fibers exit the refiner, they are flash dried with hot air in two vertical tubes in order to provide fiber twist and curl. The fibers contain approximately 10% moisture upon exiting these tubes and are ready to be cured. If the moisture content of the fibers is greater than about 10% upon exiting the flash drying tubes, then the fibers are dried with ambient temperature air until the moisture content is about 10%.
5. The nearly dry fibers are then placed on trays and cured in an air-through drying oven for a length of time and at a temperature which in practice depends on the amount of citric acid added, dryness of the fibers, etc. In this example, the samples are cured at a temperature of about 188° C. for a period of about 8 minutes. Crosslinking is completed during the period in the oven.
6. The crosslinked, individualized fibers are placed on a mesh screen and rinsed with about 20° C. water, soaked at 1% consistency for one (1) hour in about 60° C. water, screened, rinsed with about 20° C. water for a second time, centrifuged to about 60% fiber consistency, and dried to an equilibrium moisture content of about 8% with ambient temperature air.

The resulting individualized citric acid-crosslinked cellulosic fibers are refined in the above-described manner, and are formed into a sheet on an Amoco D2 scrim at a sheet/scrim Basis Weight of 150 pounds. After softening by passage over S-rolls, the sheet/scrim is suitable for use in the sanitary napkins of this invention.

Fiber C

Individualized crosslinked fibers are made by a dry crosslinking process utilizing 1,2,3,4 butane tetracarboxylic acid (BTCA) as the crosslinking agent. The individualized crosslinked fibers are produced in accordance with the hereinbefore described process of Example II with the following modifications: The slurry in step 2 of Example II contains 150 g of dry pulp, 1186 g of H$_2$O, 64 g of BTCA and 4 g of sodium hydroxide. In step 5, the fibers are cured at a temperature of about 165° C. for a period of about 60 minutes.

The resulting fibers are refined and formed into a sheet/scrim in the manner of Fiber B for use herein.

Fiber D

Individualized crosslinked fibers are made by a dry crosslinking process utilizing 1,2,3 propane tricarboxylic acid as the crosslinking agent. The individualized crosslinked fibers are produced in accordance with the hereinbefore described process of Example II with the following modifications: The slurry in step 2 of Example II contains 150 g of pulp, 1187 g of water, 64 g of 1,2,3 propane tricarboxylic acid, and 3 g of sodium hydroxide. In step 5, the fibers are cured at a temperature of about 165° C. for a period of about 60 minutes.

The resulting fibers are refined and formed into a sheet/scrim in the manner of Fiber B for use herein.

Fiber E

Individualized crosslinked fibers are made by a dry crosslinking process utilizing oxydisuccinic acid as the crosslinking agent. The individualized crosslinked fibers are produced in accordance with the hereinbefore described process of Example II with the following modififications: The slurry in step 2 of Example II contains 140 g of pulp, 985 g of water, 40 g of sodium salt of oxydisuccinic acid, and 10 ml of 98% sulfuric acid.

The resulting fibers are refined and formed into a sheet in the manner of Fiber A for use herein.

Fiber F

Individualized crosslinked fibers are made by a dry crosslinking process utilizing citric acid as the crosslinking agent and sodium sulfate as the catalyst. The individualized crosslinked fibers are produced in accordance with the hereinbefore described process of Example II with the following modifications: The slurry as described in step 2 of Example II contains 200 g of pulp, 7050 g of H$_2$O, 368 g of sodium sulfate and 368 g of citric acid. The steep pH is about 2.0. In step 5, the fibers are cured at a temperature of about 165° C. for a period of about 60 minutes.

The resulting fibers are refined as above and formed into a sheet/scrim having a Basis Weight of about 83 pounds. After softening by passage over S-rolls, the sheet is suitable for use in a pantiliner.

Fiber G

Individualized crosslinked fibers are made by a dry crosslinking process utilizing citric acid as the crosslinking agent and sodium hypophosphite as the catalyst. The individualized crosslinked fibers are produced in accordance with the hereinbefore described process of Example II with the following modifications: The slurry as described in step 2 of Example II contains 326 g of pulp, 138 g of sodium hypophosphite, 552 g of citric acid and 78 g of NaOH in 10,906 g of $H_2O$. In step 5, the fibers are cured at a temperature of about 188° C. for a period of about 6 minutes.

The resulting fibers are refined and formed into a sheet/scrim having a density of about 0.125 (at 0.1 psi pressure) and a capacity for sheep's blood of about 8.0 grams of blood/gram of sheet. Such sheets are useful at various Basis Weights in sanitary napkins and pantiliners.

In an alternate mode, the scrim used to support and strengthen the absorbent core comprising the refined fibers can comprise capillary channel fibers. Typically, such scrims comprise about 80% by weight of the capillary channel fibers and about 20% by weight of a fiber whose melting point is below that of the capillary channel fibers. KODEL fibers are suitable, for example. The scrim is prepared in standard fashion by heating to partially melt the lower-melting fibers, which, on cooling, bond the scrim together.

As noted, the layer of refined absorbent fibers is laid-down on the scrim. The resulting structure is then positioned such that the scrim is in fluid-communicating contact with the topsheet of the finished absorbent article.

EXAMPLE III

A lightweight pantiliner suitable for use between menstrual periods comprises a one gram layer of SW173 capillary channel fibers overlaying a substantially rectangular pad having a surface area of about 117 $cm^2$ and containing the sheet/scrim comprising Fiber F as the absorbent core. The capillary channel fibers are laid down substantially parallel to the machine direction of the core. The sheet/scrim plus layer of capillary channel fibers is interposed between the formed-film topsheet of U.S. Pat. No. 4,463,045 and a flexible polyethylene backsheet. Adhesive bonding of the capillary channel fibers to the topsheet is as disclosed hereinabove. The pantiliner functions to absorb vaginal discharges without the need for absorbent gelling materials.

EXAMPLE IV

A catamenial product in the form of a sanitary napkin having two flaps extending outward from its absorbent core is prepared, per the design of U.S. Pat. No. 4,687,478, Van Tilburg, Aug. 18, 1987. The absorbent core comprises a sheet/scrim having a Basis Weight of about 150 pounds, per Fiber G, herein. A 1.5 g layer of curled SW173 fibers overlays the absorbent core, with the fibers parallel to the machine direction. Assembly follows the procedure of Example II, herein. The non-glossy sheet of U.S. Pat. No. 4,463,045 is used as the topsheet.

EXAMPLE V

The sanitary napkin of Example IV is modified by needle-punching the layer of capillary channel fibers to cause a substantial number of said fibers to partially protrude downward into the absorbent core. This provides additional fluid movement in the Z-direction, i.e., out of the layer of capillary channel fibers and into the absorbent core. Alternatively, the upper layer of the absorbent core is combed or roughed such that fibers from the core extend upward into the layer of capillary channel fibers.

EXAMPLE VI

A thin pantiliner comprises a formed-film topsheet, a polyethylene backsheet and a 2.0 g layer of curled capillary channel fibers SW173. The fibers have sufficient fluid capacity in their channels to absorb a reasonable amount of vaginal discharge without the need for other absorbent materials.

EXAMPLE VII

The sanitary napkin of Example IV is modified by replacing its formed-film topsheet with a fibrous topsheet according to U.S. Pat. No. 4,636,419 or EPO 215417, respectively.

Having thus described the invention herein in great detail, some additional points are included for consideration by the formulatot. It will be appreciated that when capillary channel fibers are optionally used as a scrim onto which is wet-laid an absorbent fibrous core, some of the surfactant on the surface of the capillary channel fibers can be rinsed away. This can be readily replaced by application of additional surfactant, e.g., PEGOSPERSE.

It will be further appreciated that the in-use integrity of absorbent structures comprising the refined, curled fibers disclosed above can be further enhanced by various means. For example, ultrasonic or heat bonding can be used, especially in conjunction with the use of 10–15% by weight of thermoplastic fiber (e.g., KODEL 410 polyester) admixed with the refined fibers. In yet another method, various spot-bonding means can be employed to affix the backsheet to the core, especially over those areas to which the panty-fastening adhesive is applied.

Finally, it is to be appreciated that the preferred articles herein can employ slitted or partially slitted absorbent cores, together with curled capillary channel fibers and other extensible components which, together, provide a degree of extensibility (on the order of 15%–40%) to the article. This extensibility provides better in-use fit, comfort and decreased staining when the articles are affixed to the wearer's undergarments.

In still another mode, the central portion of the layer of capillary channel fibers can be gathered into a small "loop" or "tuft". This loop or tuft thus extends upward from the layer of capillary channel fibers to firmly contact the topsheet. Moreover, the loop or tuft is positioned centrally in the overall article, such that it can provide rapid acquisition and transport of fluid into the remaining portion of the layer of capillary channel fibers, and thence into the fluid storage layer of the article. Advantageously, such "loop" or "tuft" not only concentrates capillary channel fibers at the point where fluid impinges onto the article, but also orients the capillary channel fibers which comprise the loop or tuft substantially in the upward z-direction, thus enhancing fluid movement in the downward z-direction of the article. The following Example illustrates an absorbent article having a substantially central, z-directional tuft of capillary channel fibers.

EXAMPLE VIII

A layer of capillary channel fibers of the type disclosed herein (6-inch length) is gathered in its center to provide a slightly raised oval "tuft" having the approximate dimensions: 2-3 inches (x-direction); 1.5 inches (y-direction at widest point); and 5 mm–10 mm (z-direction). The tufted bundle of fibers can be held in its tufted configuration by any convenient means. Typically, the tuft is passed through a confining slit in a sheet of paper or hydrophilic polymer. Using the procedures disclosed herein, the tufted bundle of fibers is assembled into an absorbent article with the tuft residing approximately at the center of the overlying topsheet and with the tuft in close contact with the topsheet, as explained hereinabove. In use as a sanitary napkin, the article is positioned (e.g., intralabially) to maximize fluid uptake by the tuft. In an alternate mode, the ends of the looped fibers in the tuft are cut to provide a fleece-like, z-directional bundle of open-ended capillary channel fibers. In still another embodiment, the layer of capillary channel fibers comprising the base of the tuft is positioned wholly or partly within the wet-laid or dry-laid absorbent core of the article, rather than atop the core. In this latter embodiment, a commercially-available layered laiminate core comprising two outer tissue layers with an intermediate layer of absorbent gelling material (AGM) can be used. The capillary channels at the base of the tuft can be slipped into the internal, AGM-containing layer.

The capillary channel fibers can also be conveniently formed into a stable sheet for ease-of-manufacture into absorbent articles by means of various bonding processes. For example, about 20%–30% by weight of polyester thermoplastic fibers (e.g., KODEL 410) can be commingled with the capillary channel fibers and the resulting fibrous sheet subjected to direct thermal or through-air heating.

The refined curled cellulosic fibers can be conveniently formed into a stable sheet for ease-of-manufacture into absorbent articles by means of various bonding processes. For example, about 7%–15% by weight of polyester thermoplastic fibers (e.g., KODEL 410) can be commingled with the refined curled cellulosic fibers and the resulting fibrous sheet subjected to through-air heating or ultrasonic bonding.

Incorporation of the additional thermoplastic fibers into the capillary channel fiber layer or into the absorbent core layer, or both, offers advantages in addition to the sheet stability noted above. In particular, having the thermoplastic fibers present in the core, or in the capillary channel fiber layer, or both, allows the manufacturer to provide a seal at the periphery (at least in the crotch region) of, for example, a sanitary napkin or pantiliner, said seal providing a means whereby fluid overflow around the edges of the article is impeded, or stopped altogether.

More particularly, an article of the foregoing type can be prepared by laying-down a sheet of the refined curled cellulosic fibers containing the thermoplastic fibers onto a standard plastic backing sheet. At a position about 0.25 in. inboard from the outer edge of the sheet, a substantially continuous ultrasonic bond approximately 0.125 in. wide is formed around the periphery of the core. This not only forms the fluid-impeding seal, but also bonds the core to the backsheet.

In an alternate mode, the thermoplastic topsheet, the core containing the thermoplastic fibers and the backsheet can all be bonded together at or near the periphery by means of ultrasonic bonding. In still another mode, the layer of capillary channel fibers containing the admixed thermoplastic fibers can likewise be bonded to the core (and also to the topsheet, if desired). In still another mode, the presence of thermoplastic fibers in the core and/or in the layer of capillary fibers allows for spot bonding at various points across the article, thereby providing additional integrity when the article becomes wet.

While it will be appreciated by those familiar with the physics of fluid transport that the articles herein conveniently make use of the differences in spacings between topsheet, capillary channel fibers and core to establish a pressure gradient to draw fluids in the z-direction, other means can be employed to establish such z-direction fluid-flow gradient. For example, if the holes or spacings in the topsheet are smaller than the width of the capillary channel fibers (and such intra-fiber channel widths as wide as 90 microns may be useful for transporting relatively thick fluids such as menses), then the desired pressure gradient can be established, for example, by selecting a topsheet which is more hydrophobic than the capillary channel fibers.

What is claimed is:

1. An absorbent article having a long axis and a short axis, comprising:
   (a) a fluid permeable formed-film topsheet having a back face and a fluid-receiving front face, said topsheet having multiple openings communicating between said front face and said back face for passage of fluid through said topsheet;
   (b) an intermediate layer comprising substantially curled polymeric fibers having external intrafiber capillary channels sized to draw fluid away from the openings in said topsheet, said curled fibers being positioned such that the external intrafiber capillary channels lie substantially parallel to the long axis of said article, said intermediate layer underlying the back face of said topsheet and being in fluid-transporting contact therewith;
   (c) a fibrous moisture-absorbing structure underlying said intermediate layer and in fluid-transporting contact therewith, said moisture-absorbing structure comprising multiple non-capillary channel fibers, said non-capillary channel fibers in said moisture-absorbing structure arranged such that spacings between said non-capillary channel fibers perform a relatively strong capillary function to draw fluid away from the external intrafiber capillary channels in the curled fibers of said intermediate layer; and
   (d) a fluid impermeable backsheet underlying said moisture-absorbing structure.

2. An article according to claim 1 wherein the curled fibers in said intermediate layer are spontaneously wettable.

3. An article according to claim 1 wherein the contact between the topsheet and the intermediate layer is maintained by tensional forces between said topsheet and said intermediate layer.

4. An article according to claim 1 wherein the contact between the topsheet and the intermediate layer is maintained by bonding means.

5. An article according to claim 1 wherein portions of the curled fibers in said intermediate layer at least partially protrude through said topsheet.

6. An article according to claim 1 wherein portions of the curled fibers in said intermediate layer partially protrude into said topsheet.

7. An article according to claim 1 wherein said moisture-absorbing structure comprises a wet-laid sheet of refined, stiffened, curled cellulosic fibers.

8. An article according to claim 7 wherein said moisture-absorbing structure comprises a wet-laid sheet of refined, stiffened, curled, chemically cross-linked cellulosic fibers.

9. An article according to claim I wherein portions of the curled fibers in said intermediate layer at least partially protrude into said moisture-absorbing structure.

10. An article according to claim 9 wherein portions of the curled fibers in said intermediate layer at least partially protrude into said topsheet and into said moisture-absorbing structure.

11. An absorbent article having a long axis and a short axis, comprising:
  (a) a fluid permeable fibrous topsheet having a back face and a fluid-receiving front face, said topsheet having multiple interfiber openings communicating between said front face and said back face for passage of fluid through said topsheet;
  (b) an intermediate layer comprising substantially curled polymeric fibers having external intrafiber capillary channels sized to draw fluid away from the openings in said topsheet, said curled fibers being positioned such that the external intrafiber capillary channels lie substantially parallel to the long axis of said article, said intermediate layer underlying the back face of said topsheet and being in fluid-transporting contact therewith; and
  (c) a fibrous moisture-absorbing structure underlying said intermediate layer and in fluid-transporting contact therewith, said moisture-absorbing structure comprising multiple non-capillary channel fibers, said non-capillary channel fibers in said moisture-absorbing structure arranged such that spacings between said non-capillary channel fibers perform a relatively strong capillary function to draw fluid away from the external intrafiber capillary channels in the curled fibers of said intermediate layer.

12. An article according to claim 11 wherein the curled fibers in said intermediate layer are spontaneously wettable.

13. An article according to claim 11 wherein portions of the curled fibers in said intermediate layer partially protrude into said topsheet.

14. An article according to claim 11 wherein said moisture-absorbing structure comprises a wet-laid sheet of refined, stiffened, curled cellulosic fibers.

15. An article according to claim 14 wherein said moisture-absorbing structure comprises a wet-laid sheet of refined, stiffened, curled, chemically cross-linked cellulosic fibers.

* * * * *